(12) United States Patent
Capart

(10) Patent No.: US 10,092,312 B2
(45) Date of Patent: Oct. 9, 2018

(54) DEVICE FOR CHEMICALLY ASSISTED DISSECTION

(71) Applicant: AuXin Surgery SA, Louvain la Neuve (BE)

(72) Inventor: Gilles Capart, Brussels (BE)

(73) Assignee: AUXIN SURGERY SA, Louvain la Neuve (BE)

( * ) Notice: Subject to any disclaimer, the term of this patent is extended or adjusted under 35 U.S.C. 154(b) by 227 days.

(21) Appl. No.: 14/889,084

(22) PCT Filed: May 7, 2014

(86) PCT No.: PCT/EP2014/059332
§ 371 (c)(1),
(2) Date: Nov. 4, 2015

(87) PCT Pub. No.: WO2014/180902
PCT Pub. Date: Nov. 13, 2014

(65) Prior Publication Data
US 2016/0081706 A1    Mar. 24, 2016

(30) Foreign Application Priority Data

May 7, 2013   (EP) .................................... 13166898
Dec. 19, 2013   (EP) .................................... 13198443

(51) Int. Cl.
*A61B 17/3203*   (2006.01)
*A61M 5/24*   (2006.01)
(Continued)

(52) U.S. Cl.
CPC ....... *A61B 17/3203* (2013.01); *A61M 5/1407* (2013.01); *A61M 5/2448* (2013.01); *A61B 2090/0816* (2016.02)

(58) Field of Classification Search
CPC ........ A61M 2005/31598; A61M 5/284; A61M 5/2066; A61M 5/2448; A61M 5/31596
See application file for complete search history.

(56) References Cited

U.S. PATENT DOCUMENTS 2,176,042 A  *  10/1939  Pittenger ............... A61J 1/2096
                                                                    206/221
3,340,873 A       9/1967   Solowey
(Continued)

FOREIGN PATENT DOCUMENTS

EP          0858775 A      8/1998
WO       WO 95/32015     11/1995
(Continued)

OTHER PUBLICATIONS

Office Action in European Patent Application No. 14721889.5, dated Mar. 21, 2017.

*Primary Examiner* — Bradley J Osinski
(74) *Attorney, Agent, or Firm* — Knobbe Martens Olson & Bear LLP

(57) ABSTRACT

A device and a method for delivering a solution to tissues and/or organs is described. The solution contains at least one solvent and at least one solute. The device includes at least one chamber which contains sodium 2-mercaptoethanesulfonate in powder form. The method includes the steps of dissolving the solute in the solvent inside the device. The resulting solution is delivered immediately to tissues and/or organs to facilitate dissection.

4 Claims, 17 Drawing Sheets

(51) Int. Cl.
*A61M 5/14* (2006.01)
*A61B 90/00* (2016.01)

(56) References Cited

U.S. PATENT DOCUMENTS

| | | | | |
|---|---|---|---|---|
| 3,757,779 | A | * | 9/1973 | Rovinski ............... A61M 5/284 |
| | | | | 604/190 |
| 3,785,379 | A | | 1/1974 | Cohen |
| 4,822,340 | A | * | 4/1989 | Kamstra ............. A61M 5/2066 |
| | | | | 604/135 |
| 4,959,215 | A | * | 9/1990 | Sauerbier ............. A61K 9/0019 |
| | | | | 424/422 |
| 5,281,198 | A | | 1/1994 | Haber et al. |
| 5,637,087 | A | * | 6/1997 | O'Neil et al. ........ A61M 5/282 |
| | | | | 604/82 |
| 5,728,738 | A | * | 3/1998 | Engel ................... A61K 31/185 |
| | | | | 514/706 |
| 5,807,323 | A | * | 9/1998 | Kriesel ............. A61M 5/14526 |
| | | | | 604/232 |
| 2009/0171311 | A1 | | 7/2009 | Genosar et al. |
| 2009/0299328 | A1 | | 12/2009 | Mudd et al. |

FOREIGN PATENT DOCUMENTS

| WO | WO 2005/032515 A1 | 4/2005 |
|---|---|---|
| WO | WO 2009/009274 A2 | 1/2009 |
| WO | WO 2012/064761 A2 | 5/2012 |

* cited by examiner

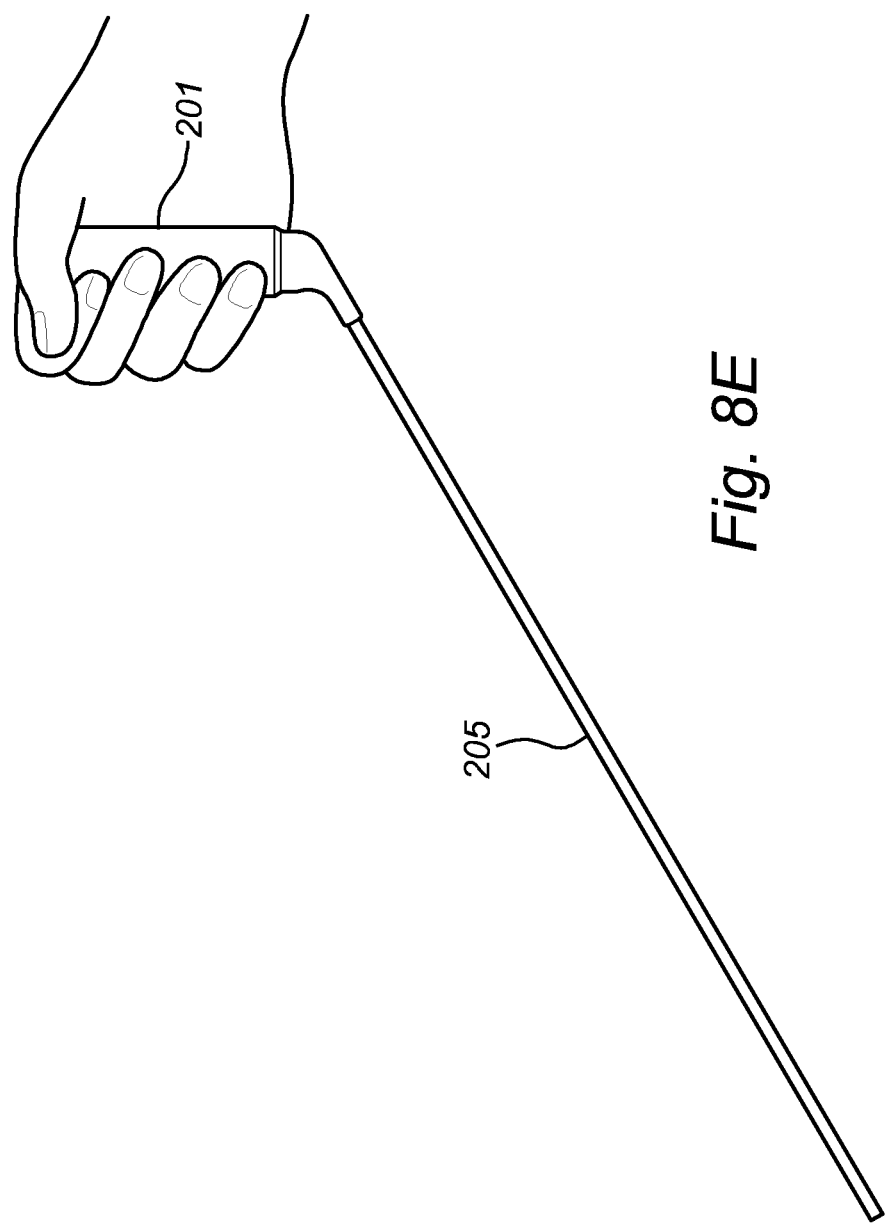

DEVICE FOR CHEMICALLY ASSISTED DISSECTION

CROSS-REFERENCE TO RELATED APPLICATIONS

This application is the U.S. National Phase under 35 U.S.C. § 371 of International Application PCT/EP2014/059332, filed May 7, 2014, which claims priority to EP 13166898.0, filed May 7, 2013 and EP 13198443.7, filed Dec. 19, 2013.

FIELD OF THE INVENTION

The present invention relates to a device and a method for delivering a solution to biological tissues. In particular, the invention relates to devices for mixing and delivering chemicals for biological tissues separation and/or assisting said separation.

BACKGROUND

Dissection instruments have found ample usage as manual surgical instruments in multiple surgical fields including abdominal surgery, orthopedics and neurosurgery. Their action is to mechanically dissect tissues. Dissectors assist in the detachment of normal tissues to enable appropriate penetration through the soft tissue layers or in the detachment of various pathological tissues from healthy tissues.

The detachment of tissues using standard mechanical tissue dissectors can be quite tedious and is often responsible for long surgical operations. In addition, post-operative complications may occur in some surgical procedures such as impairing the function of the remaining tissues, nerves or veins, hemorrhage, infections and recurrence. These complications result from the difficulties that surgeons may encounter in highlighting the cleavage planes, detaching tissue layers and obtaining hemostasis. An important technical progress in this field would be to facilitate the detachment of tissues, increase the success rate of cyst or tumor removals, avoid damage of remaining surrounding organs, reduce blood loss and post-operative adhesions, thereby reducing operation duration, reduce medical costs of such operations as well as health risks for patients.

It is known that when applied at the cleavage plane, sodium-2-mercaptoethane sulfonate or Mesna breaks the molecular bonds between tissue layers, thereby facilitating tissue separation. Specifically, Mesna breaks disulfide bonds of polypeptide chains and proteins. However, nowadays for tissue separation, Mesna is only available in liquid form. A major drawback of Mesna solutions is their instability as mentioned in U.S. Pat. No. 5,728,738. The liquid form is highly prone to oxidation and is therefore highly unstable especially in presence of metals. Therefore, it is common to store Mesna solutions in low iron glass containers under nitrogen blanket with stabilizers and anti-oxidants. When being used, the practitioner has to transfer the solution from glass containers to a delivery device or to a tube in order to bring the solution in contact with the desired tissue. This step increases contamination risk at the dissection site and increases surgery time. This is in addition to the high chances of oxidation of the stored Mesna solution thereby having a reduced Mesna activity when used for assisting surgery.

Other drawback of the Mesna in liquid form which is available today resides in the absence of concentration choice. In some procedures, larger quantities and/or different concentration of Mesna, from that readily available in commercial glass vials, are needed Indeed the practitioner can only dilute the Mesna which is available in liquid form and cannot use higher Mesna concentrations if required. This makes making the use of said vials tedious or inadequate. As mentioned in U.S. Pat. No. 5,728,738, Mesna solutions available are stabilized by addition of pH adjustment agents, additives such antioxidants and stabilizing agents thereby avoiding oxidation and/or the degradation of Mesna when the Mesna solution is stored. Addition of such agents presents a considerable risk for patient's health and increases the cost of said Mesna solutions. In addition, commercial solutions are not isotonic and may damage exposed cells when applied topically.

One of the objectives of the invention is to overcome at least part of the above mentioned problems. The invention aims at providing a device and method for increasing the shelf life of Mesna before use, optimizing the stability of the delivered Mesna in liquid form and for optimizing the delivery of said Mesna in liquid form to the target location at the desired concentration, volume and quality for surgical applications. In addition, the present invention aims at providing the user with a possibility to choose the concentration of the Mesna solution to be used. In addition, the invention aims at lowering the costs of the Mesna solution provided to the user.

SUMMARY

The present invention provides a device for delivering a solution comprising at least one solvent and at least one solute. Preferably, the solution consists of one solute and one solvent. The solute is a mucolytic agent in powder form. Said mucolytic agent is sodium 2-mercaptoethanesulfonate, known as Mesna, in powder form. Preferably, the device comprises at least one chamber which comprises sodium 2-mercaptoethanesulfonate in powder form. Preferably said solvent is a sterile physiological saline solution or saline water wherein the content of NaCl is adjusted to make the solution isotonic. The use of isotonic solution in surgery is advantageous as it prevents the exposed cells in the surgery site from damage.

In a preferred embodiment, the device comprises a first chamber for housing the solute, a second chamber for housing the solvent and at least one outlet suitable to be in fluid communication with at least one of the chambers; said chambers are separated from each other by at least one disruptable separation means and are in fluid communication with each other upon disruption of said separation means thereby forming the solution. In a preferred embodiment, said device comprises at least one pressure means for manually applying a pressure on the first chamber walls and/or the second chamber walls thereby delivering the solution to said tissues and/or organs. Preferably, the wall of the first chamber walls and/or the second chamber is made of a flexible material.

In a preferred embodiment, the separation means comprises a spatial separation between the first chamber and the second chamber. Said separation means can also be devoid of spatial separation between the first chamber and the second chamber. Preferably, the separation means comprises at least one disruption means for disrupting said separation means.

In a preferred embodiment, the device comprises a single chamber for housing the solute, at least one outlet suitable to be in fluid communication with the single chamber and at least one connection means which is in fluid communication with said single chamber thereby connecting the single chamber to a solvent source.

The device according to any embodiment of the invention is connectable to and/or controlled by an electrically driven mechanical system for the delivery of Mesna solution to the target location.

In a preferred embodiment, the device consists of a single chamber for housing the solute. The device is provided with at least one outlet and is suitable to be connected—via said outlet—to a solvent reservoir in order to produce a solution that can be used with high pressure liquid delivery device. Said solvent is preferably saline water wherein the NaCl is adjusted to make said solution isotonic. For instance, the solvent reservoir is connectable to a solvent jet surgery system known to the person skilled in the art as water jet surgery system. The reservoir with the Mesna solution replaces the physiological water bag present in conventional known water jet surgery systems, also called hydrosurgery.

The device according to the invention is suitable to be used as a chemically assisted tissue dissector instrument. Said device is suitable to be connected to any surgical dissector known to the person skilled in the art provided with fluid connection for dispensing at the active edge of said surgical dissector. The device allows the topical and local instillation of a chemical solution to facilitate the mechanical dissection and separation of tissue.

In a preferred embodiment, the device comprises at least one air vent for air evacuation of the device and/or air insertion into the device. The device is designed to be hand held and hand manipulated by the operator.

The invention further provides a kit comprising sodium 2-mercaptoethanesulfonate is in powder form, a solvent for dissolving said sodium 2-mercaptoethanesulfonate and a device according to any of the preceding claims wherein said device comprises at least said sodium 2-mercaptoethanesulfonate is in powder form. In a preferred embodiment, the solvent is saline water wherein the content of NaCl is adjusted to make the solution isotonic.

The present invention further provides a method for weakening inter-tissues and/or organs adhesion to facilitate dissection by delivering a solution comprising at least one solvent and at least one solute to tissues and/or organs. Preferably, the solution consists of one solute and one solvent. The method comprises the steps of dissolving said solute in said solvent thereby obtaining the solution and delivering the obtained solution to said tissues and/or organs; said solute is a mucolytic agent in powder form. The solution is preferably immediately delivered after being obtained. Preferably, said mucolytic agent is sodium 2-mercaptoethanesulfonate also known as Mesna. More preferably Mesna is used in powder form. Preferably said solvent is a sterile physiological saline solution wherein the content of NaCl is adjusted to make the solution isotonic.

Immediately delivered after being obtained means that the solution is delivered at most 24 hours, preferably at most 12 hours, more preferably at most 6 hours, even more preferably at most 4 hours, most preferably at most 30 min, even most preferably at most 10 min after dissolving the solute in the solvent. In a further preferred embodiment, said solution is delivered at most 5 min, preferably at most 4 min, more preferably at most 3 min, most preferably immediately, i.e. 0 min, after dissolving the solute in the solvent. Preferably, the solution is solution is delivered in droplets form having a predetermined volume.

In a preferred embodiment, the solute and/or the solvent are devoid of antioxidants and/or stabilizing agents.

In one embodiment, the method further comprises the steps of providing a device comprising two chambers as described above, disrupting the separation means of the device thereby obtaining the solution, and delivering the obtained solution through the outlet of the device to a target location.

In another embodiment, the method comprises the steps of providing a device comprising a single chamber as described above, connecting said device and more in particular said single chamber to an external solvent source, inserting the solvent into said single chamber thereby obtaining the solution, i.e. Mesna solution, and delivering the obtained solution through the outlet of the device to a target location. Preferably, the solution consists of one solute and one solvent.

In another embodiment, the method comprises the steps of providing a device comprising a single chamber as described above suitable to be connected to a reservoir containing a solvent, inserting the solute into said reservoir thereby obtaining the solution, i.e. Mesna solution, connecting said reservoir containing said Mesna solution to a water jet surgery system, and delivering the obtained solution to a target location. Preferably, the solution consists of one solute and one solvent. Said delivery is made through a delivery means of water jet surgery system thereby, delivering Mesna solution to the target location at high pressure. Said delivery means is selected from the group comprising: a surgical device, a high pressure pump, a delivery tube, an applicator or any combination thereof.

The invention further provides for the use of a mucolytic agent in hydrosurgery. Said mucolytic agent is sodium 2-mercaptoethanesulfonate, preferably in powder form. The invention further provides hydrosurgery method comprising the steps of: connecting a first container comprising the solute to a second container comprising the solvent; transferring at least partially the content of the first container into the second container thereby dissolving the solute in the solvent and obtaining the solution; disconnecting the first container from the second container, and delivering the obtained solution to said tissues and/or organs, wherein said solute is sodium 2-mercaptoethanesulfonate in powder form.

The invention also provides a kit comprising at least one first container which is sealed by a disruptable membrane and comprising the solute, at least one second container comprising the solvent and at least one disrupting device for disrupting the disruptable membrane of the first container wherein said solute is sodium 2-mercaptoethanesulfonate in powder form. In a preferred embodiment, the solvent is saline water wherein the content of NaCl is adjusted to make the solution isotonic. The use of isotonic solution in surgery is advantageous as it prevents the exposed cells surrounding the surgery site from damage.

The device of the invention is connectable to dissection instruments, via a luer lock fluid connection for instance. The device enables the controlled instillation of the synthetic sulfur compound Mesna during tissue dissection directly in contact with the tissue to be detached thus reducing its diffusion. Mesna facilitates the mechanical tissue separation by the surgical dissector. The chemical compound for instillation is located in the device and thus forms an integral part of the device. Mesna is stored in the device in powder form before use to take advantage of the superior stability properties of the solid powder form compared to the formulated solution.

The device and the method of the invention present several advantages. Oxidation of Mesna solution before delivery is avoided as said solution is prepared immediately before said delivery. Another advantage is the absence of antioxidants and/or stabilizing agents, the use of which is not required as the solution is prepared immediately prior use. This reduces the risk of potential side effects from the use of such additives and the cost of the prepared solution. The invention further provides a maximized sterility of the delivered solution and thereby of the surgery and/or the treatment. In addition, the invention provides for a controlled delivery of the Mesna solution which can be delivered at the practitioner's will and at the required time. It avoids cumbersome manipulations of solutions from glass vials in order to obtain the desired concentration and volume. Furthermore, the invention offers to the user the possibility to choose the concentration of Mesna solution to be used.

The device and the method of the invention are easy to use and facilitate tissue dissection while preserving healthy tissue and organ functions. Observable benefits are to reduce the damage to the remaining tissues or organs, a reduction of pre- and post-operative bleeding, a reduction of post-operation adhesions, a reduction in surgical procedure time and an increased surgeon satisfaction. In addition, the invention allows decreasing hospital stay duration, preventing post-operative complications and allows decrease disease recurrence. Another advantage provided by the invention is the easy use and handling of the device. Said device is inexpensive and simple to produce.

BRIEF DESCRIPTION OF THE FIGURES

FIG. 8E shows a perspective view of the use of the device shown in FIG. 8A.

DETAILED DESCRIPTION

Figure 1:
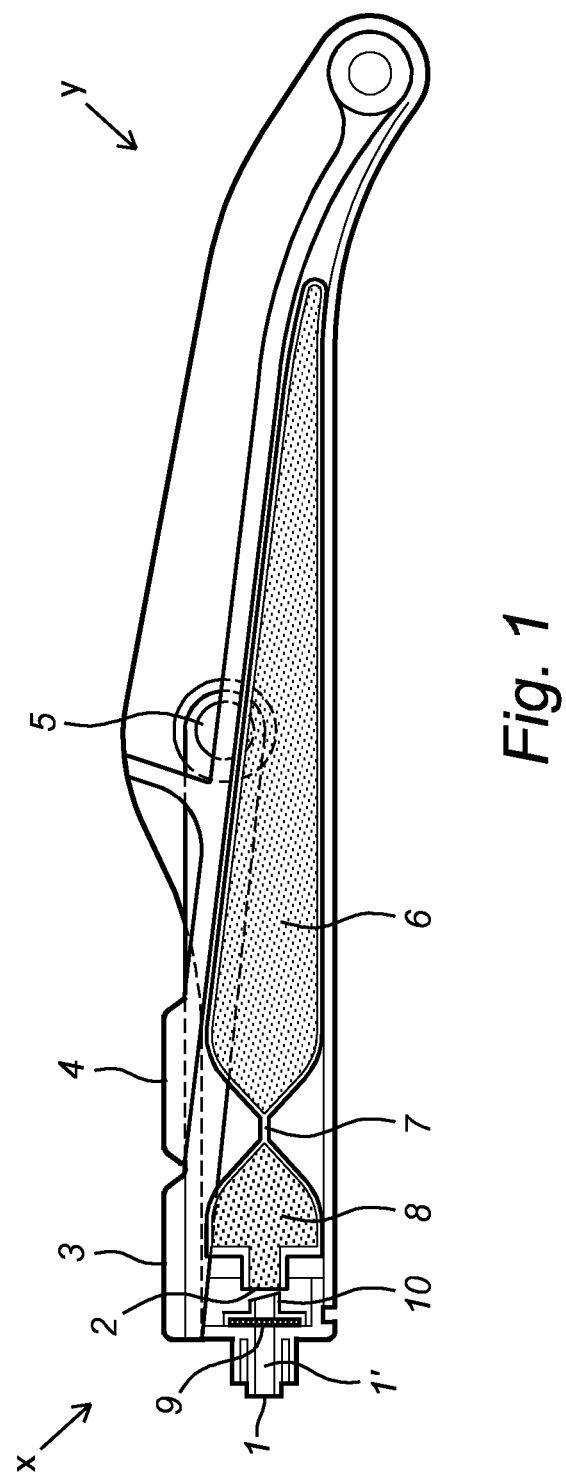
FIG. 1 shows a first embodiment of the device according to the invention.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

As used herein, the following terms have the following meanings: "A", "an", and "the" as used herein refers to both singular and plural referents unless the context clearly dictates otherwise. By way of example, "a compartment" refers to one or more than one compartment.

"About" as used herein referring to a measurable value such as a parameter, an amount, a temporal duration, and the like, is meant to encompass variations of +/−20% or less, preferably +/−10% or less, more preferably +/−5% or less, even more preferably +/−1% or less, and still more preferably +/−0.1% or less of and from the specified value, in so far such variations are appropriate to perform in the disclosed invention. However, it is to be understood that the value to which the modifier "about" refers is itself also specifically disclosed.

"Comprise," "comprising," and "comprises" and "comprised of" as used herein are synonymous with "include", "including", "includes" or "contain", "containing", "contains" and are inclusive or open-ended terms that specifies the presence of what follows e.g. component and do not exclude or preclude the presence of additional, non-recited components, features, element, members, steps, known in the art or disclosed therein.

The recitation of numerical ranges by endpoints includes all numbers and fractions subsumed within that range, as well as the recited endpoints.

The expression "% by weight" (weight percent), here and throughout the description unless otherwise defined, refers to the relative weight of the respective component based on the overall weight of the formulation.

The present invention provides a device for delivering a solution comprising at least one solvent and at least one solute. Preferably, the solution consists of one solute and one solvent. Said solute is a mucolytic agent in powder form. In a preferred embodiment, said mucolytic agent is sodium 2-mercaptoethanesulfonate known as Mesna. In a preferred embodiment, Mesna is used in a powder form. In a preferred embodiment, said solute is saline water wherein the NaCl content is adjusted to make the solution isotonic. The solution, also called herein Mesna solution, the mixture, the Mesna mixture or the solution is shortly prepared prior use.

Preferably, the device comprises at least one control means which provides for the control of the solution volume delivered and flowing out of the device.

In a preferred embodiment, the device comprises a first chamber for housing the solute, a second chamber for housing the solvent and at least one outlet suitable to be in fluid communication with at least one of the chambers; said chambers are separated from each other by at least one disruptable separation means and are in fluid communication with each other upon disruption of said separation means.

Preferably, the separation means comprise a spatial separation between the first chamber and the second chamber. This means that when the device is not in use, the chambers do not share any common element, such as membranes and/or walls. In this embodiment, when the device is used, at least one of said chambers is movable towards the other chamber and/or both chambers are movable towards each other. One of the advantages of this design is that it offers the possibility to fill the chambers separately from each other in a sterile environment. Assembling the device can then later be performed in a non-sterile environment. After assembling the device, an extra sterilization step can be performed.

The first chamber and the second chamber can be also attached to each other by said separation means. This means that when the device is in use, it is not required to move at least one of the chambers towards the other chamber. Said chambers are fluidly connected to each other upon removal of the separation means.

Preferably, the device comprises at least one disruption means for disrupting said separation means. Preferably, the device further comprises a disruptable sealing membrane positioned between the outlet and the chamber which is suitable to be in fluid communication with said outlet.

In a preferred embodiment, the device comprises a single chamber for housing the solute, at least one connection means for fluidly connecting said device to an external solvent source and at least one outlet suitable to be in fluid communication with said single chamber. Preferably, said solute is a mucolytic agent in powder form. This embodiment provides a device which is easy to use, allows delivering high Mesna solution volumes and can be used in any operating room surgery. The device further presents a very low production cost.

Preferably, the connection means connects said device, more in particular the single chamber of the device, to a solvent source. The connection means can be any means known to the person skilled in the art. Said means can be an opening or a tube which is connectable to a solvent source or line or the outlet of the device itself. The device preferably comprises a plunger, or any similar system known to the person skilled in the art, for the suction of the solvent from the solvent source into the single chamber of the device through the connection means.

The solvent volume which will be inserted into the single chamber of the device can be a predefined amount that is fully inserted in said chamber. The practitioner can hence select the concentration of the Mesna solution that is deemed required for the target location, for the type of the tissue to be separated and/or the type of the intervention. Said concentration will of course depend on the amount of Mesna powder provided in the single chamber of the device and the solvent volume introduced by the practitioner into said chamber. In a preferred embodiment, the device is provided with an information sheet comprising at least an indication of the Mesna powder amount contained in the single chamber of the device.

After obtaining the Mesna solution, at the desired concentration, inside the single chamber of the device, the connection between the single chamber and the solvent source can be removed so as to prevent insertion of more solvent into said chamber. The solution can then be delivered to the target.

In a preferred embodiment, the device comprises a single chamber for housing the solute suitable to be connected to a solvent reservoir in order to prepare a solution. Said reservoir is connectable to a solvent jet surgery system known to the person skilled in the art as water jet surgery system. Said reservoir replaces the physiological water bag present in conventional known water jet surgery systems. The single chamber is provided with the required fluid connection for connecting it to a solvent reservoir. Said connection is known to the person skilled in the art. The invention allows delivering Mesna solution contained in said reservoir at high pressure for assisting surgery. A multifunction device is thereby achieved, which combines the advantages of water jet surgery, including injection of the liquid and/or dissection by means of liquid, with the advantages of the delivered Mesna solution. In particular, dissection is made possible at lower jet pressures, minimizing the risks of accidental damage to the surrounding tissues and extending the range of possible applications of water jet surgery. Hence, the device according to the invention makes it possible to inject liquid and/or the Mesna solution, obtained in the single chamber, to the target location with high pressure thereby lifting the target away from other surrounding tissues. Device for water jet surgery are known to the person skilled in the art and are for instance disclosed in U.S. Pat. No. 5,116,313 and US 2009/0069805.

After obtaining the Mesna solution, at the desired concentration, inside said reservoir, the device is connected to the water jet surgery system. Delivery of Mesna solution under pressure to the target location can be initiated. In a preferred embodiment, the device, more in particular the single chamber containing Mesna solution, replaces the physiological water bag present in conventional known water jet surgery systems. The water jet surgery system preferably comprises a delivery means selected from the group comprising: a surgical device, a high pressure pump, a delivery tube or applicator or any combination thereof. The Mesna solution is delivered via said delivery means to the target location. The surgical device is as described above.

The present invention further provides a method for weakening inter-tissues and/or organs adhesion by delivering a solution comprising at least one solvent and at least one solute to tissues and/or organs. Preferably, the solution consists of one solute and one solvent. The method comprises the steps of dissolving said solute in said solvent thereby obtaining the solution, and delivering the obtained solution to said inter-tissues and/or organs. Preferably, the solute is a mucolytic agent in powder form. Preferably said solvent is a sterile physiological saline solution.

In a preferred embodiment, the method further comprises the steps of providing a device comprising two chambers as described above, disrupting the separation means of the device thereby obtaining the solution, and delivering the obtained solution through the outlet of the device to a target location.

In another embodiment, the method comprises the steps of providing a device comprising a single chamber as described above, connecting said device and more in particular said single chamber to an external solvent source, inserting the solvent into said single chamber thereby obtaining the solution, i.e. Mesna solution, and delivering the obtained solution through the outlet of the device to a target location.

In another embodiment, the method comprises the steps of providing a device comprising a single chamber as described above, inserting the solvent into said single chamber thereby obtaining the solution, i.e. Mesna solution, connecting said device and more in particular said single chamber to a water jet surgery system, and delivering the obtained solution to a target location. Preferably, the solution consists of one solute and one solvent. Said delivery is made through a delivery means of water jet surgery system thereby, delivering Mesna solution to the target location at high pressure. Said delivery means is selected from the group comprising: a surgical device, a high pressure pump, a delivery tube, an applicator or any combination thereof.

The method according to any embodiment of the invention provides for the controlled delivery of Mesna solution. Said controlled delivery might be performed using control means of the device and/or using an electrically driven mechanical system. Said system can be a syringe driver, a syringe pump or any other system known to the person skilled in the art. Said system is preferably controlled by the practitioner using a pedal connected to the electrically driven mechanical system. This is advantageous as it provides the practitioner with a high hands freedom level required for instance for laparoscopic surgery also called minimal invasive surgery. Indeed, said practitioner will be able to use both hands for operations other than handling the device for delivering Mesna solution to the target location.

It is to be understood that for all the embodiments of the device and/or the method of the present invention, the solute amount contained in the device and/or the solvent volume are selected such as the solute concentration in the solution is of from 5% to 50%, preferably of from 10% to 40%, more preferably from 15% to 30%, most preferably from 20% to 25% or any value comprised in between the mentioned ranges. In a preferred embodiment, the solvent is saline water wherein the content of NaCl is adjusted to make the solution isotonic.

The device according to any embodiment of the present invention comprises at least one sterilization microfilter positioned between the outlet of the device and the chamber which is suitable to be in fluid communication with said outlet. Preferably said microfilter is a membrane made of polyethylene terephtalate, polyamide, polyethersulfone, nylon or any other suitable material. In a preferred embodiment, the pore size is from 0.1 to 3 µm, preferably from 0.15 to 2 µm, more preferably from 0.2 to 1 µm, most preferably about 0.22 µm. The presence of said microfilter further enhances the sterility of the solution and/or ensures the instillation of the sterile solution of the device, i.e. Mesna solution, during dissection. In a preferred embodiment, said microfilter has an additional ventilation membrane to remove air bubbles during dispensing and letting air in the chamber to compensate for liquid volume dispensed. In a preferred embodiment, the pore size of the ventilation membrane is from 0.01 to 0.05 µm, preferably about 0.02 µm. The ventilation membrane is preferably made of polytetrafluoroethylene or any other suitable material.

It is to be understood that for all the embodiments of the device and/or the method of the present invention, the Mesna in powder contained in the device is sterilized, preferably by gamma irradiation or X-ray. The irradiation is preferably performed at least at 20 kGy, preferably at least 25 kGy, more preferably at least 30 kGy and at most 50 kGy, preferably at most 40 kGy.

The outlet of the device, according to any embodiment of the present invention, is suitable to be connected to a surgical device or to a delivery tube. Said outlet might be connected via a luer lock mechanism to said surgical device. The surgical device can be a dissector instrument, known to the person skilled in the art, which primary function is tissues separation in surgery through mechanical action. Said dissector is a general manual surgical instrument used in gynecology, ENT surgery, orthopedics, neurosurgical and all other surgical procedures where tissues need to be separated. Said dissectors are stainless steel or titanium instruments with different hooks and curves, such as long-medium, short beveled hook, hook with ball, straight and curved, big and small size versions. The dissectors may be fitted with internal capillary tube for dispensing the fluid at their active edge. The shape of the dissector to be used in surgery depends on the application and area. Many dissectors are re-usable or disposable, in plastic, stainless steel, titanium or other metals. The dissector can also be fitted with a cavity and a second capillary tube for the suction of the excess liquids and Mesna solution, as commonly used for removing excess liquids from the operating field during the procedure that would otherwise prevent complete vision of the field. In a preferred embodiment, said surgical device or delivery tube can be combined with suction and/or suction/irrigation devices used in open and minimally invasive surgery. For minimally invasive surgery, said surgical device or delivery tube can be inserted in the instrument channel of suction/irrigation devices.

The device, according to any embodiment of the present invention, is connectable to and/or controllable by an electrically driven mechanical system for the delivery of Mesna solution to the target location. Said system can be a syringe driver, a syringe pump or any other system known to the person skilled in the art. Said system is preferably controlled by the practitioner using a pedal connected to the electrically driven mechanical system. This is advantageous as it provides the practitioner with a high hands freedom level required for instance for laparoscopic surgery also called minimal invasive surgery. Indeed, said practitioner will be able to use both hands for operations other than handling the device for delivering Mesna solution to the target location.

The device, according to any embodiment of the present invention can also be hand held and hand manipulated by the operator. Where required, the device is further provided with a plunger which is used by the operator for delivering said Mesna solution. Said plunger is slidably engaged into one chamber of the device.

The device, according to any embodiment of the invention, is a single-use device. By preference, it is a single-use chemically assisted tissue dissector indicated for the cleavage and separation of tissue layers to facilitate various surgical procedures, including abdominal surgery, gynecology, orthopedics and otoneurosurgery.

The device and/or the method according to any embodiment of the present invention, allows mixing Mesna powder with the solvent shortly prior use thereby making it possible to provide a Mesna solution having a maximum Mesna activity as oxidation of said Mesna is reduced compared to Mesna solutions stored for a long time prior use. Said Mesna solution is prepared and/or delivered to the target at most 24 hours, preferably at most 12 hours, more preferably at most 6 hours, even more preferably at most 4 hours, most preferably at most 30 min, even most preferably at most 10 min after dissolving the solute in the solvent. In a further preferred embodiment, said solution is delivered at most 5 min, preferably at most 4 min, more preferably at most 3 min, most preferably immediately, i.e. 0 min, after dissolving the solute in the solvent. In a preferred embodiment, the solvent is suitable for dissolving the mucolytic agent in powder form. Preferably said solvent is a sterile physiological saline solution. In a preferred embodiment, the device is designed to contain 5 to 60 ml, preferably 10 to 50 ml, more preferably 12 to 40 ml, most preferably 15 to 30 ml of solvent or any volume comprised within the mentioned ranges. Preferably, the device is designed to contain about 20 ml of solvent.

The present invention further provides a kit comprising Mesna in powder form, a solvent for dissolving said Mesna and a device according to any embodiment of the invention. In a preferred embodiment, the device comprises said Mesna in powder form and/or said solvent. In a preferred embodiment, the solvent is saline water wherein the content of NaCl is adjusted to make the solution isotonic. The kit further comprises a leaflet provided with user's instructions and/or information on the Mesna and/or the solvent and/or the device of said kit.

The different embodiments of the device will now be described with reference to the accompanying figures.

Referring to FIG. 1, a first embodiment of the device is shown. The device comprises a first chamber 8 housing a first substance and a second chamber 6 housing a second substance. In FIG. 1, the first chamber comprises the first substance in powder form, i.e. the solute and the second chamber comprises the liquid in which said first substance will be dissolved, i.e. the solvent. In a preferred embodiment, said first substance in powder form is Mesna. The chambers are separated from each other by a disruptable separation means. In this embodiment, the chambers are also attached to each other by the same disruptable separation means which is in this case a disruptable membrane 7. The first chamber 8 is sealed by a disruptable sealing membrane 2. The proximal end X of the device is provided with an outlet 1 and an outlet tube 1' for guiding the mixture out of the device. The outlet tube 1' is movable and its distal end Y is suitable to disrupt the sealing membrane 2 of the first chamber 8. Said distal end of the outlet tube 1' might have a pointed shape as shown in FIG. 1 or might be of any other type and/or shape suitable to disrupt the sealing membrane 2. The device further comprises a microfilter 9 positioned between the outlet 1 of the device and the first chamber 8 which is suitable to be in fluid communication with said outlet 1. Preferably, the microfilter is integrated with and/or within the outlet tube 1'. Said microfilter enhances the sterility and prevents contamination of the device and the solution and/or powder contained therein. In a preferred embodiment, said microfilter is made of polyethylene terephtalate, nylon, polyethersulfone or polyamide membrane.

The device shown in FIG. 1 is further provided with a disruption means for disrupting the separation means, i.e. disruptable membrane 7. Said disruption means comprises a lever 4, a trigger 3 and a gear ratchet 5, preferably a gear with locking ratchet. The trigger 3 is movable from a position in which its proximal end X is in contact with the device, called down position, to a position in which the proximal end X of the trigger 3 is not in contact with the device, called up position. The lever 4 is in contact with the gear ratchet 5 and also in contact with one of the chambers, preferably with the chamber 6 which is at the distal end Y of the device, more preferably with the device containing the liquid solvent. With this design, the movement of the trigger 3 leads to the rotation of the gear ratchet 5 which in turn moves the lever 4, thereby applying a pressure on the chamber 6.

Figure 2:
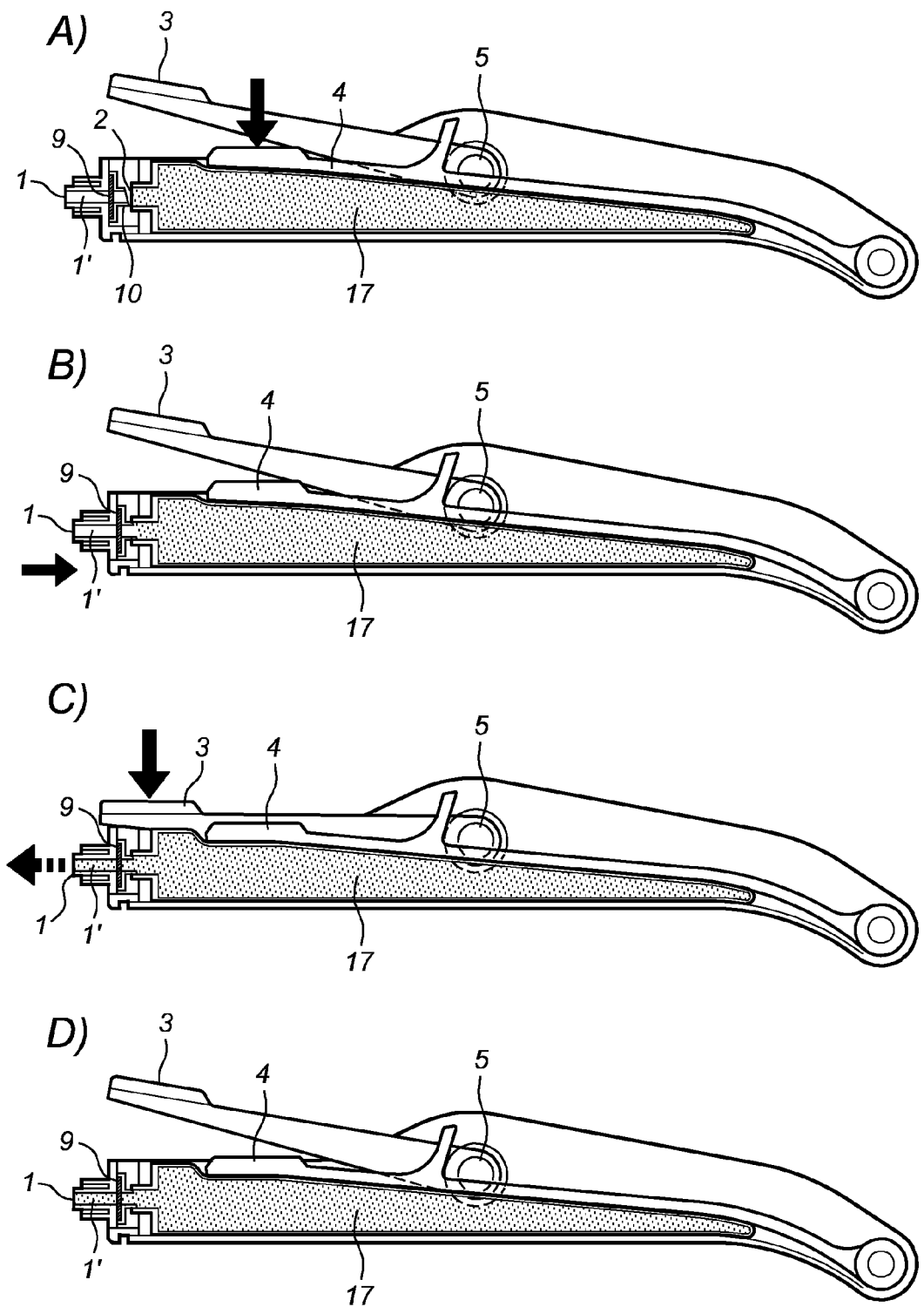
FIG. 2 A to D shows the steps of use of the device presented in FIG. 1.

In use, the user moves the trigger 3 to the up position as shown in FIG. 2A. Said trigger 3 might be fixed to the device and/or to the lever 4 by a snap fit system, or any other removable fixation means known to the person skilled in the art, when the device is not in use (FIG. 1). Then, the user moves the trigger 3 from its up position towards its down position as shown by the arrow in FIG. 2A. By doing so, the trigger 3 and/or gear ratchet 5 move the lever 4 in the same direction as the movement of the trigger 3, thereby applying a pressure on the liquid chamber 6. Said movement and/or pressure leads to the disruption of the separation means, i.e. disruptable membrane 7 thereby fluidly connecting both chambers, as shown by element 17. The content of both chambers 6 and 8 are brought together thereby dissolving the solute in the solvent and obtaining the solution as shown in FIG. 2A. The device can also be designed such as the disruption of the separation means caused by a pressure applied by the user on the lever 4 of the device (as shown by the arrow in FIG. 2A).

Afterwards, the user pushes the outlet tube 1' towards the distal end Y of the device as shown by the arrow in FIG. 2B. The outlet tube 1' might be pushed by connecting the outlet 1 of the device to any other device such as a surgical tissue dissector. Said outlet tube might also be twisted by connecting the outlet 1 of the device to any other device such as a surgical tissue dissector. Said outlet tube 1' will disrupt the sealing membrane 2 and will be in fluid contact with the fluidly connected chambers 17 of the device FIG. 2B. In the next step, the user moves the trigger 3 from its up position towards its down position as shown by the continued arrow of FIG. 2C. The lever 4 will then be moved in the same direction as the movement of the trigger 3, thereby applying a pressure on the liquid chamber 6 leading to the flow of the solution out of the device through the outlet tube and the outlet 1 of the device as shown by the discontinued arrow in FIG. 2C. The gear ratchet 5 might be provided with a spring which is extended when the trigger 3 moves towards its down position. Said spring forces the trigger 3 to go back to its up position (shown in FIG. 2D) whenever the uses not applying any force on the trigger 3 in order to move it from the up position to the down position.

The device is simple to use and offers a rapid system for dissolving the solute in the solvent. The device is also practical as it is suitable to be manually held by the user such as said holding is comparable to a pen holding wherein the index finger is moving the trigger 3 of the device.

The device is provided with control means for the control of fluid volume flowing out of the device. Said control means comprises the trigger 3, the gear ratchet 5 and the lever 4 which are designed and/or positioned such as a predetermined volume of solution is flowing out of the device with each movement of the trigger 3 from its up position to its down position. In this way, the user can have a control over the amount of fluid flowing out of the device, thereby avoiding any excess of delivered solution volume. In addition, the user will be provided with a control over the time at which the fluid is flowing out of the device. These possibilities are not offered by the devices of the prior art.

Figure 3:
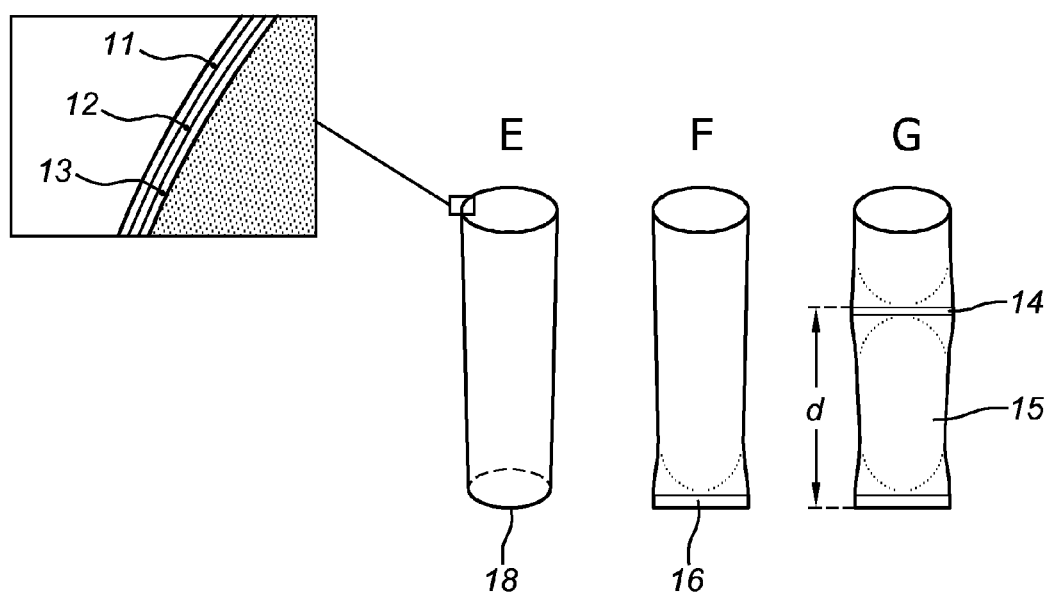
FIG. 3 E to G shows the steps for obtaining the chambers of the device presented in FIG. 1.

FIG. 3 shows the steps for obtaining the chambers of the device presented in FIG. 1. A sleeve or a tube 18 (FIG. 3E) is permanently sealed at one end 16. A second seal 14 is then created at a distance d from the permanent seal 16 thereby creating a chamber. The second created seal 14 is a frangible seal and corresponds to the separation means, i.e. disruptable membrane 7 of the device shown in FIG. 1. The distance d is dependent on the diameter of the tube 18 and/or on the solvent's volume or the amount of powder that will be introduced in the created chamber. In a preferred embodiment, the permanent seal 16 and the frangible seal 14 are created by heat sealing the tube 18 at desired positions.

In a preferred embodiment, the sleeve or tube membrane is made of a laminate material as shown in the enlarged view of FIG. 3E. Said laminate material comprises at least an adhesive layer 12 having two surfaces, wherein one surface is covered by a layer 10 of high heat seal resistant material and the other surface is covered by a layer 13 which is preferably made from polypropylene or polyethylene or a combination thereof. In a preferred embodiment, the high heat seal resistant material layer 10 is the outer surface of the tube 18 and the layer 13 made from polypropylene or polyethylene or a combination thereof is the inner surface of the tube 18 (FIG. 3E). In a preferred embodiment, the laminate material is a polyethylene laminate, more preferably, polychlorotrifluorethylene laminate.

In a preferred embodiment, the trigger and/or the lever and/or the gear with locking ratchet and/or the outer walls of the device are made of injectable plastic material. In a preferred embodiment, the separation means and/or the sealing membrane are made of aluminium laminate.

Figure 4:
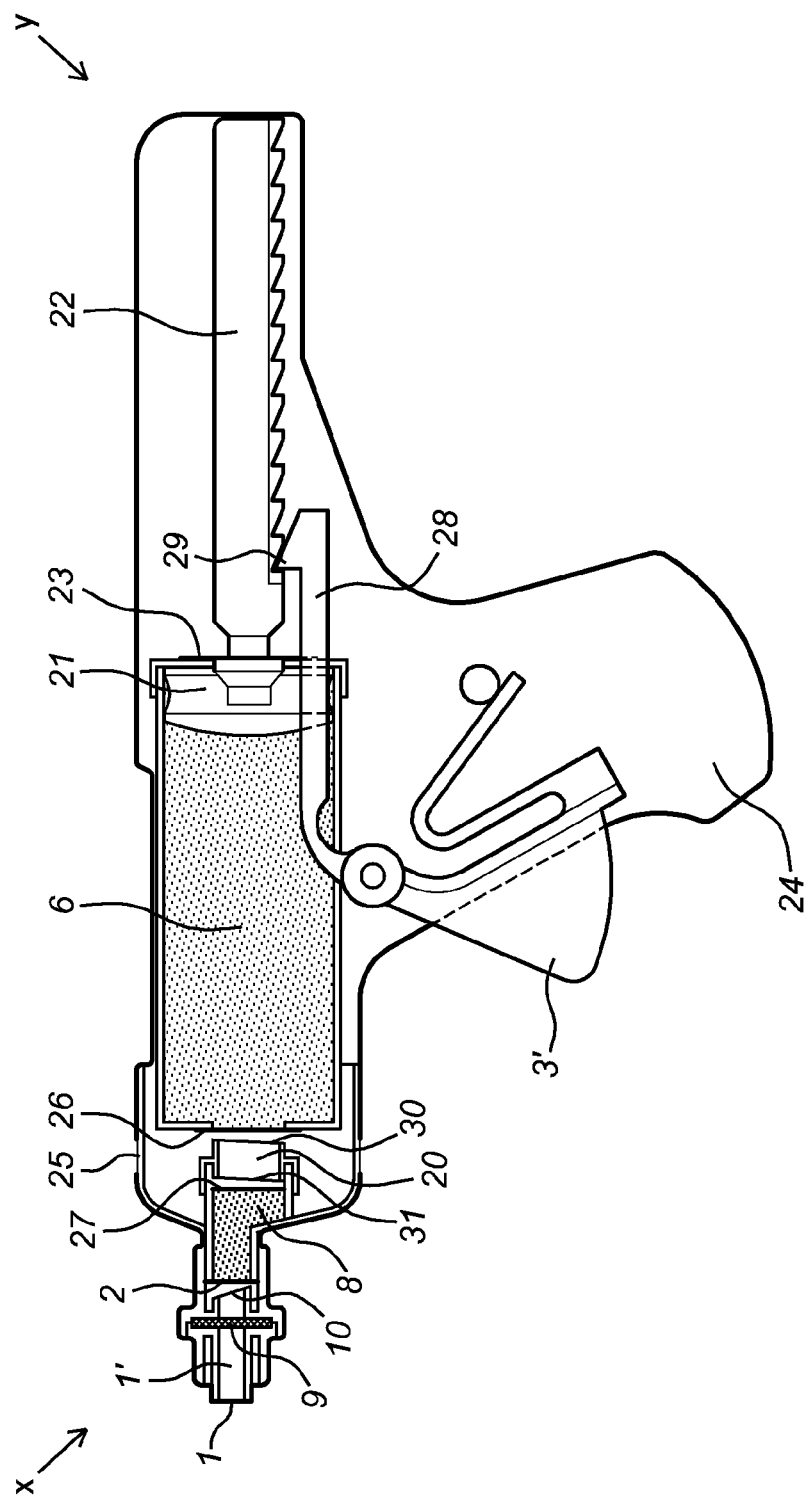
FIG. 4 shows a second embodiment of the device according to the invention.

Referring to FIG. 4, a second embodiment of the device is shown. The device comprises a first chamber 8 housing a first substance and a second chamber 6 housing a second substance. In FIG. 4, the first chamber comprises the first substance in powder form, i.e. the solute and the second chamber comprises the liquid in which said first substance will be dissolved, i.e. the solvent. In a preferred embodiment, said first substance in powder form is Mesna. At least one of the walls of each chamber is at least partially made of a disruptable membrane. The chambers are separated from each other by a separation means which comprises a spatial separation between the first chamber and the second chamber. This means that the chambers are spatially separated from each other. The separation means further comprises the disruptable membranes 26, 27 of said chambers. In this embodiment, at least one of said chambers is movable towards the other chamber which can be movable or non-movable. Preferably said movement is a sliding movement. The first chamber 8 is sealed by a disruptable sealing membrane 2 which is not forming a part of the separation means. The proximal end X of the device is provided with an outlet 1 and an outlet tube 1' for guiding the mixture out of the device. The outlet tube 1' is movable and its distal end Y is suitable to disrupt the sealing membrane 2 of the first chamber 8. Said distal end of the outlet tube 1' might have a pointed shape as shown in FIG. 4 or might be of any other type and/or shape suitable to disrupt the sealing membrane 2. The device further comprises a microfilter 9 positioned between the outlet 1 of the device and the first chamber 8 which is suitable to be in fluid communication with said outlet 1. Preferably, the microfilter is integrated with and/or within the outlet tube 1'. Said microfilter enhances the sterility and prevents contamination of the device and the solution and/or powder contained therein. In a preferred embodiment, said microfilter is made of polyethylene terephtalate, polyethersulfone, nylon or polyamide membrane. The device is also provided with a handle 24 via which the device is hold in a way similar to a pistol hold.

The device shown in FIG. 4 is further provided with a disruption means for disrupting the separation means. Said disruption means comprises a piercing means 20, trigger 3', a linear ratchet 22 and a plunger 21. The piercing means is positioned between the first chamber 8 and the second chamber 6; preferably said piercing means 20 is positioned between the disruptable membranes 26, 27 of the chambers which are part of the separation means of the device. Said piercing means 20 is provided with at least two opposed piercing members 30, 31 for piercing and disrupting the disruptable membranes 26, 27 of the first and the second chambers. The piercing means 20 might be fixed to the first chamber 8 as shown in FIG. 4. Alternatively, said piercing means 20 might be fixed to the second chamber 6 or to the walls of both chambers. The trigger 3' is suitable to be squeezed or pushed towards the handle 24 of the device. Said trigger 3' is connected to a sliding block 28 having a drive tooth 29 suitable to engage a tooth of the linear ratchet 22 (FIG. 4). When the device is not used, the trigger 3' is in "off position" in which it is not pushed in the handle 24 and the drive tooth 29 is engaging the most proximal tooth of the linear ratchet 22 as shown in FIG. 4. Preferably, the shape of the proximal end X of the linear ratchet 22 is form fitting the plunger 21 distal end Y. Said plunger 21 is positioned between the linear ratchet 22 and one of the chambers of the device, preferably the second chamber 6 containing the solvent as shown in FIG. 4. The distal end Y of the plunger 21 might be provided with a disruptable sealing membrane 23 (FIG. 4).

Figure 5:
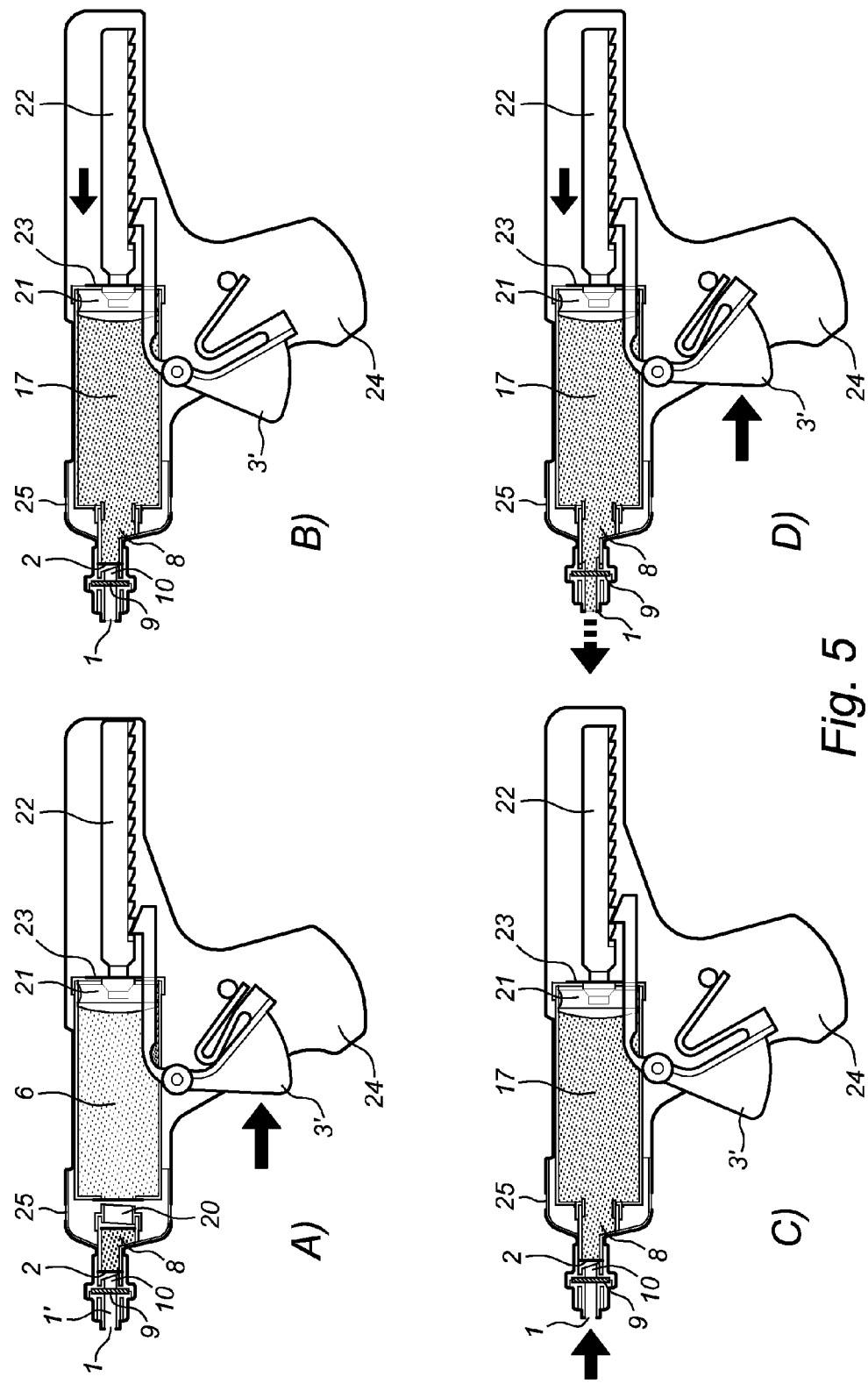
FIG. 5A to D shows the steps of use of the device presented in FIG. 4.

In use, the user moves the trigger 3' from its "off position" towards the handle 24 of the device as shown by the arrow in FIG. 5A. The movement of the trigger 3' leads to the movement of the sliding block 28 towards the distal end Y of the device thereby leading to the movement, i.e. sliding, of the drive tooth 29 which will engage the neighboring teeth of the linear ratchet 22. By neighboring teeth we refer the teeth positioned at the distal end Y of the ratchet teeth that is engaged by the drive tooth 29. The linear ratchet 22 will then be moved towards the proximal end X of the device and will disrupt the disruptable sealing membrane 23 of the plunger 21. The movement of the linear ratchet 22 continues leading to the engagement of the proximal end X of said ratchet 22 in the distal end Y of the plunger 21 as shown in FIG. 5A. The movement of the linear ratchet 22 towards the proximal end X of the device continues thereby moving the second chamber 6 in the same direction and forcing said chamber to come in contact with the piercing member 20 which will pierce and disrupt the disruptable membrane 27 of the second chamber 6 which is part of the separation means of the device (FIG. 5B). The piercing means 20 is designed to pierce and disrupt the disruptable membrane of the second chamber 6 without being completely inserted inside said chamber 6 as shown in FIG. 5B. The disruption of the disruptable membrane 27 of the second chamber 6 is performed by the piercing member 30 which is in close vicinity of said disruptable membrane 27. The movement of the linear ratchet 22 continues thereby forcing the piercing means 20 to pierce and disrupt the disruptable membrane 26 of the first chamber 8 as shown in FIG. 5B. It is to be understood that the piercing and the disruption of the disruptable membranes 26, 27 of the chambers can performed subsequently or simultaneously. In the latter case, the second chamber 6 is moved towards the proximal end X of the device until the opposed piercing members 30, 31 of the piercing means 20 are in contact with the disruptable membranes 26, 27 of the chambers. By continuing the movement of the second chamber towards the proximal end X of the device, both disruptable members are simultaneously disrupted.

The disruption of the disruptable membrane 26 of the first chamber 8 is performed by the piercing member 31 which is in close vicinity of said disruptable membrane 26 and which is opposing the piercing member 30 used for disruption of the membrane of the second chamber 6.

After disruption of the disruptable membranes 26, 27, the chambers 8, 6 will be fluidly connected to each other 17. The respective content of said chambers will merge. The solute will dissolve in the solvent thereby obtaining a solution as shown in FIG. 5B. In a next step, the user pushes the outlet tube 1' towards the distal end Y of the device as shown by the arrow in FIG. 5C. Said outlet tube 1' will disrupt the sealing membrane 2 and will be in fluid contact with the fluidly connected chambers 17 of the device FIG. 5D. The outlet tube 1' might be pushed and/or twisted by connecting the outlet 1 of the device to any other device such as a surgical tissue dissector. Afterwards, the user pushes and/or squeezes further the trigger 3' towards the handle 24 of the device as shown by the arrow in FIG. 5D thereby leading to the flow of the solution out of the device through the outlet 1.

In a preferred embodiment, the device is provided with at least one air vent 25 for evacuating air from the device when the first chamber 8 is moved towards the second chamber 6. Said air vent 25 is preferably provided at the proximal end X of the device outer walls more preferably at the level of the second chamber or the piercing member 20 when starting from the distal end Y of the device towards its proximal end.

The device is simple to use and offers a rapid system for dissolving the solute in the solvent. The device is also practical as it is suitable to be manually held by the user such as said holding is comparable to a pistol holding wherein the index finger is moving the trigger 3' of the device.

The device is provided with control means for the control of fluid volume flowing out of the device. Said control means comprises the trigger 3', the sliding block 28 and the linear ratchet 22 which are designed and/or positioned such as a predetermined volume of solution is flowing out of the device with each movement of the drive tooth 29. By movement of the drive tooth, we refer to the sliding of said drive tooth by which the drive tooth 29 will engage the neighboring teeth of the linear ratchet 22. In this way, the user can have a control over the amount of fluid flowing out of the device, thereby avoiding any excess of delivered solution volume. In addition, the user will be provided with a control over the time at which the fluid is flowing out of the device. These possibilities are not offered by the devices of the prior art.

Figure 6A:
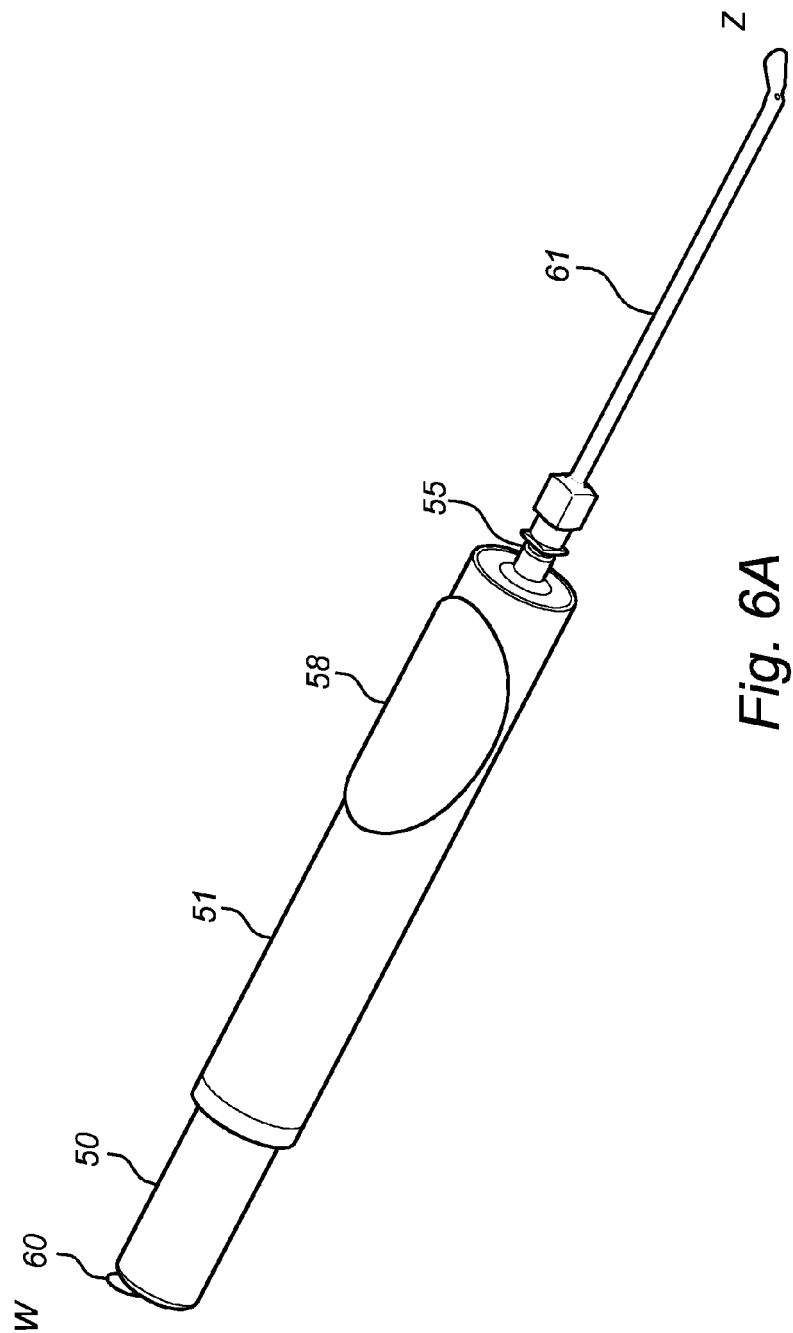
FIG. 6A shows a perspective view of a device according to a third embodiment of the invention.

Referring to FIG. 6A, a third embodiment of the device is shown. The device comprises a first chamber 50 for housing the solute, i.e. Mesna in powder form; a second chamber 51 for housing the solvent and at least one outlet 55 for delivering the solution. Said outlet is suitable to be in fluid communication with at least one of the chambers. On FIG. 6A, the outlet 55 is suitable to be in fluid communication with the second chamber 51. Said outlet 55 is covered by a removable cap (not shown) when the device is not used.

The chambers are separated from each other by at least one separation means comprising at least one disruptable separation means (52, 53 in FIG. 6B) and are in fluid communication with each other upon disruption of said disruptable separation means. At least one of the walls of each chamber is at least partially made of a disruptable membrane thereby forming the disruptable separation means.

Figure 6B:
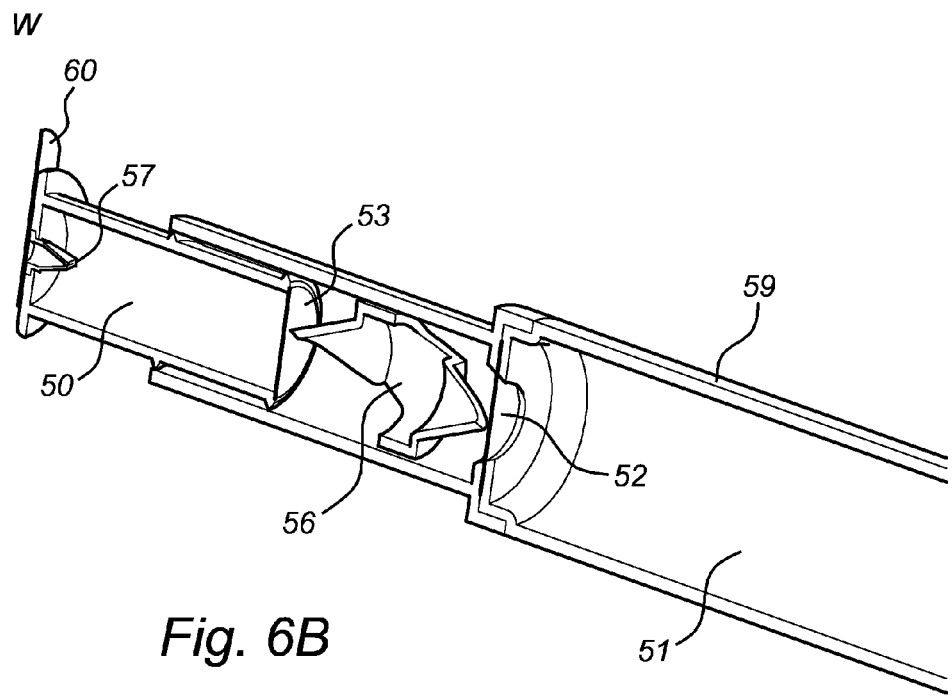
FIG. 6B shows a cross section view of the device of FIG. 6A wherein the chambers are not pierced.

FIG. 6B shows the details of the separation means. The chambers are separated from each other by a separation means which comprises a spatial separation between the first chamber 50 and the second chamber 51. This means that the chambers are spatially separated from each other and when the device is not in use, the chambers do not share any common element, such as membranes and/or walls. The separation means further comprises the above mentioned disruptable membranes 52, 53 of said chambers. At least one of said chambers is movable towards the other chamber which can be movable or non-movable. Said movement can be a sliding and/or a rotating movement. By preference, the first chamber 50 is movable towards the second chamber 51 which is non-movable. The first chamber 50 is sealed by a non-disruptable sealing membrane 60 which is not forming a part of the separation means.

The device is further provided with a disruption means 56 for disrupting the disruptable separation means, more in particular for disrupting the disruptable membranes 52 and 53. Said disruption means comprises at least one piercing means 56. The piercing means is positioned between the first chamber 50 and the second chamber 51. Preferably said piercing means 56 is comprised in the separation means and is positioned between the disruptable membranes 52, 53 of the chambers which are part of the separation means of the device. Said piercing means 56 is provided with at least two opposed piercing members for piercing and disrupting the disruptable membranes 52, 53 of the first and the second chambers (FIG. 6B). In a preferred embodiment, the disruptable membranes 52, 53 are made of aluminium laminate.

Figure 6C:
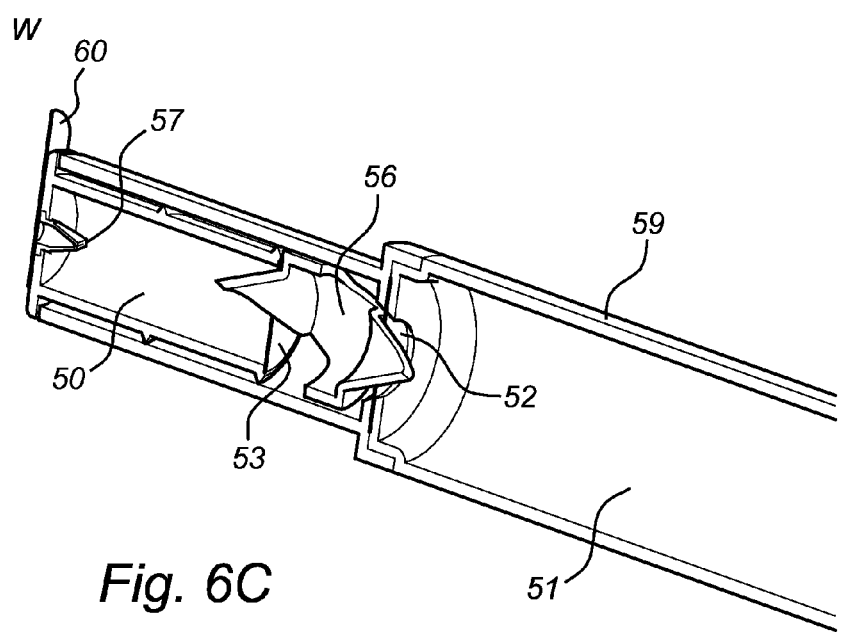
FIG. 6C shows a cross section view of the device of FIG. 6A wherein the chambers are pierced.
Figure 6D:
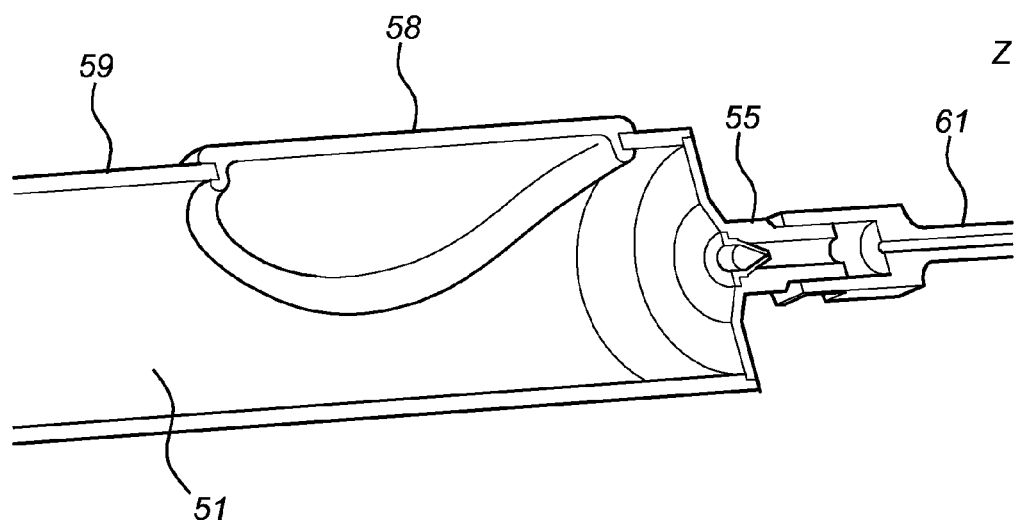
FIG. 6D shows a closer cross section view of the pressure means and the outlet of the device of FIG. 6A.

In a preferred embodiment, the device is provided with at least one air vent 57 for evacuating and/or inserting air from the device. Said air vent is covered by non-disruptable sealing membrane 60 when the device is not used (FIG. 6B). Said air vent 57 is preferably provided at the distal end W of the device outer wall. FIG. 6C shows a cross section view of the device wherein the chambers are pierced by the piercing means 56. Details of the proximal end of the device are shown on FIG. 6D. The proximal end Z of the device is provided with an outlet 55 for expelling the Mesna solution out of the device. Said outlet 55 is covered by a removable cap (not shown) when the device is not used.

In use, the user moves the first chamber 50 towards the second chamber 51. The movement leads to the disruption of the disruptable membranes 52, 53 by the piercing means 56 (FIG. 6C). The content of the first and the second chambers will merge to obtain the Mesna solution in which the solute is dissolved in the solvent. The device can be further agitated or shacked to further mix the solvent and the solute. Afterwards, the removable cap is removed thereby uncovering the outlet 55. The foil tab 60 is then removed for allowing air to replace the volume of the dispensed solution. The outlet of the device can then be used for direct delivery of the Mesna solution to the target or can be connected to any other suitable device such as a dissector 61. It is to be understood that the air vent 57 and the tab 60 can be replaced by an air permeable membrane.

In a preferred embodiment, the device comprises at least one pressure means 58 for manually applying a pressure on the first chamber walls and/or the second chamber walls thereby delivering the solution to said tissues and/or organs. The pressure means 58 is preferably visible to the user. The pressure means 58 can be a flexible button. Preferably, the second chamber is fitted with the pressure means 58. Said pressure means 58 is suitable for the application of a manual pressure thereby delivering the solution to said tissues and/or organs. The uncovered air vent 57 admits air when the flexible wall of the chamber returns to its stable position.

In a preferred embodiment, the invention provides a method for weakening inter-tissues and/or organs adhesion by delivering a solution comprising at least one solvent and at least one solute to tissues and/or organs. The method comprises the steps of providing a device as described above; disrupting the separation means thereby obtaining the solution wherein the solute is dissolved in said solvent; and immediately delivering the obtained solution to said tissues and/or organs; wherein said solute is sodium 2-mercaptoethanesulfonate in powder form.

In a preferred embodiment, the solution is delivered in droplets form by applying a manual pressure on pressure means 58 and thereby on the fluidly connected chambers wall. In this embodiment, the control means of the device comprise the pressure means 58. The droplets have a predetermined volume which is of from 50 to 200 µl, preferably from 60 to 150 µl, more preferably from 70 to 100 µl. In this way the user is capable of hand manipulating the device for directly delivering the Mesna solution from the device to the desired location and in desired volumes. The design, the manufacture and the use of the device are simple thereby saving costs and working time. Furthermore, the device offers a possibility to control the amount of fluid flowing out of the device, thereby avoiding any excess of delivered solution volume. In addition, the user will be provided with a control over the time at which the fluid is flowing out of the device. These possibilities are not offered by the devices of the prior art.

Figure 7A:
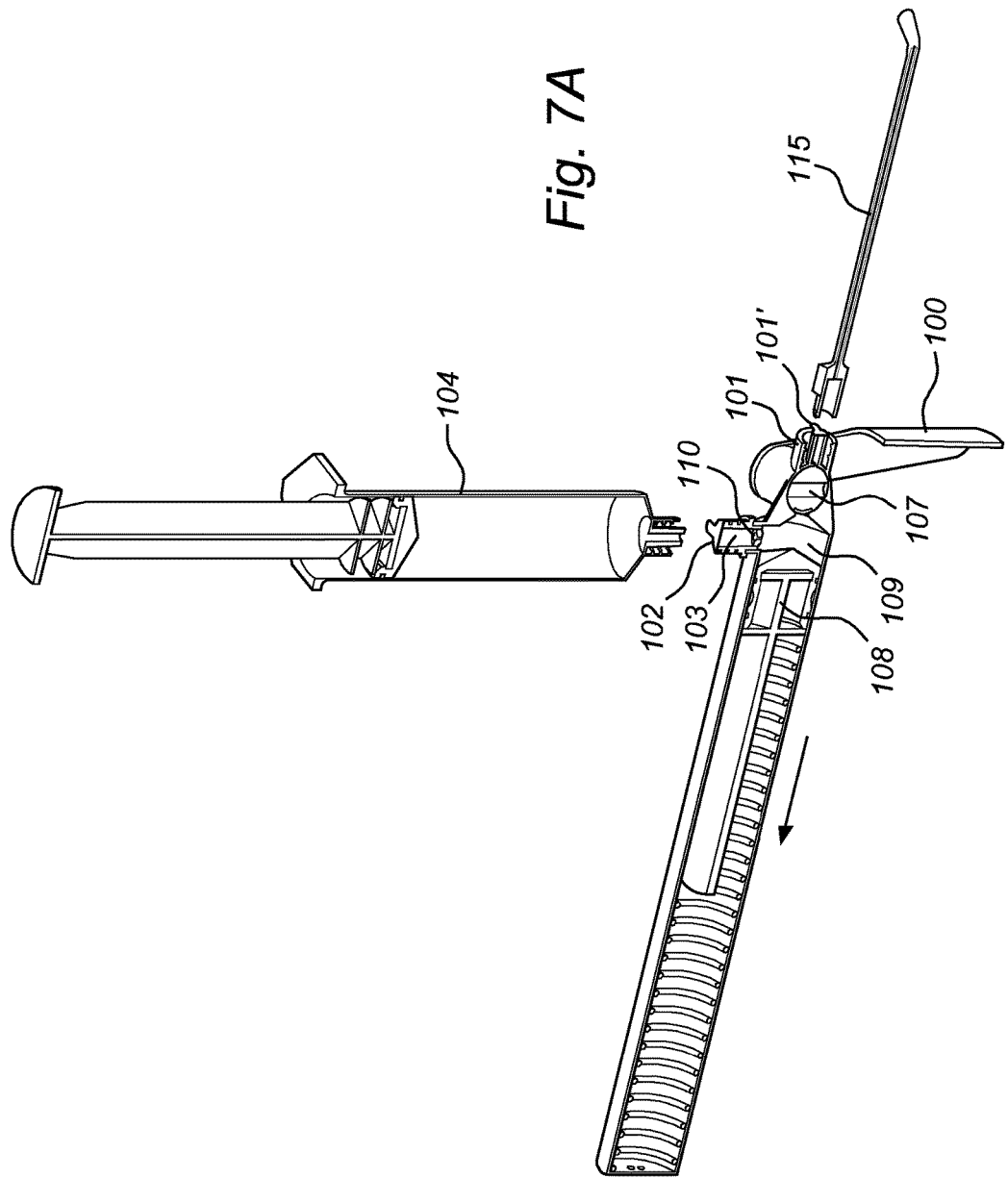
FIG. 7A shows a cross section view of a device according to a fourth embodiment of the invention. Said device is closed position.

Referring to FIG. 7A, a fourth embodiment of the device is shown. The device comprises a single chamber 109 for housing the solute, a spring piston 108, an outlet 101 and a connection means 103. The outlet 101 is suitable to be in fluid communication with the single chamber 109 of the device and can be covered by a removable cap or a foil 101' when the device is not used. Said device can have any shape and is preferably cylindrical as shown in FIG. 7A. The connection means 103 can be an opening or a tube positioned at the outer wall of the device. The connection means 103 can be covered by a removable cap or a foil 102 when the device is not used. Said connection means 103 is in fluid communication with the single chamber of said device.

Preferably, the device further comprises a lumen 107 positioned between the single chamber 109 and the outlet tube 106 of the device. Said lumen 107 is movable between an open position in which said lumen 107, the single chamber 109 and the outlet tube 106 are in fluid communication with each other and a closed position (FIG. 7A) in which said lumen 107, single chamber 109 and the outlet tube 106 are not in fluid communication with each other. Movement of the lumen can be ensured by placing said lumen into a pivotable section of the device. Said section is pivotable by manipulating a lever 100 provided to the outer wall of the device as shown in FIG. 7A. Alternatively, the lumen 107 can be movable by simply placing on the outer wall of the device a movable button which mechanically moves said lumen between the open and the closed position. Movement of the lumen can also be performed using a piston valve, a rotary valve or any other means known to the person skilled in the art.

The device is connectable to a solvent source via the connection means 103. Said solvent source can be a second device 104 as shown in FIG. 7A. The connection means 103 connects the second device to the single chamber 109 of the device. The second device 104 is used for injecting the solvent into the single chamber of the device thereby obtaining the desired solution, i.e. Mesna solution, at the desired concentration. The second device 104 is preferably provided with volume graduation indications. Said second device can be a prefilled syringe as shown in FIG. 7A or any other device known by the person skilled in the art. The device according to this embodiment offers the user the possibility to choose the solvent volume to be added to the single chamber of the device and thereby of the concentration of Mesna solution to be used.

The connection means 103 is in fluid contact with the single chamber when the second device is connected to said device. The connection means 103 is provided with a one way valve 110 thereby preventing the content of the single chamber from flowing outside the device when the second device is disconnected.

Figure 7B:
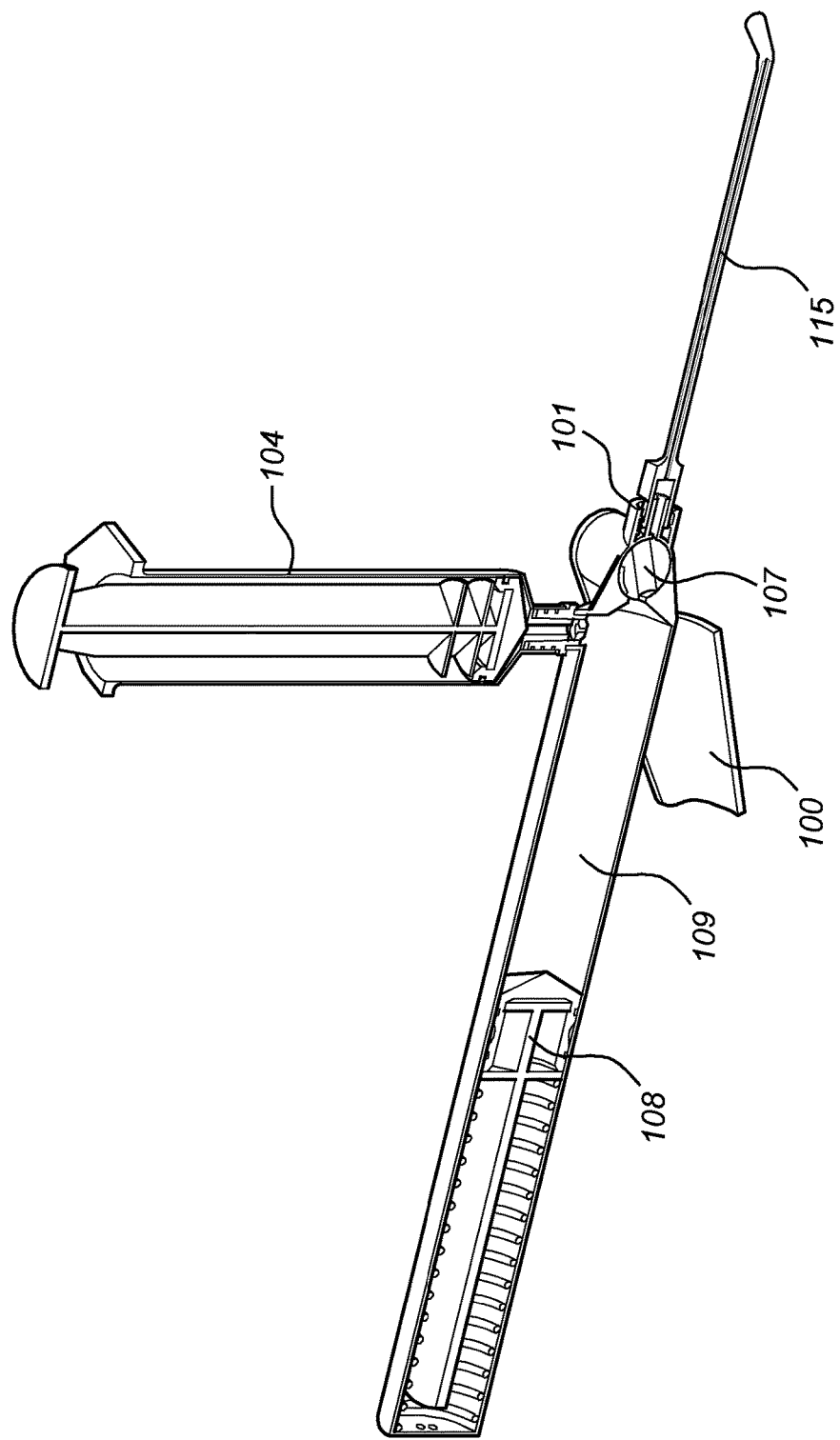
FIG. 7B shows a cross section view of the device shown in FIG. 7A wherein a second device, here a syringe, is connected to the device.
Figure 7C:
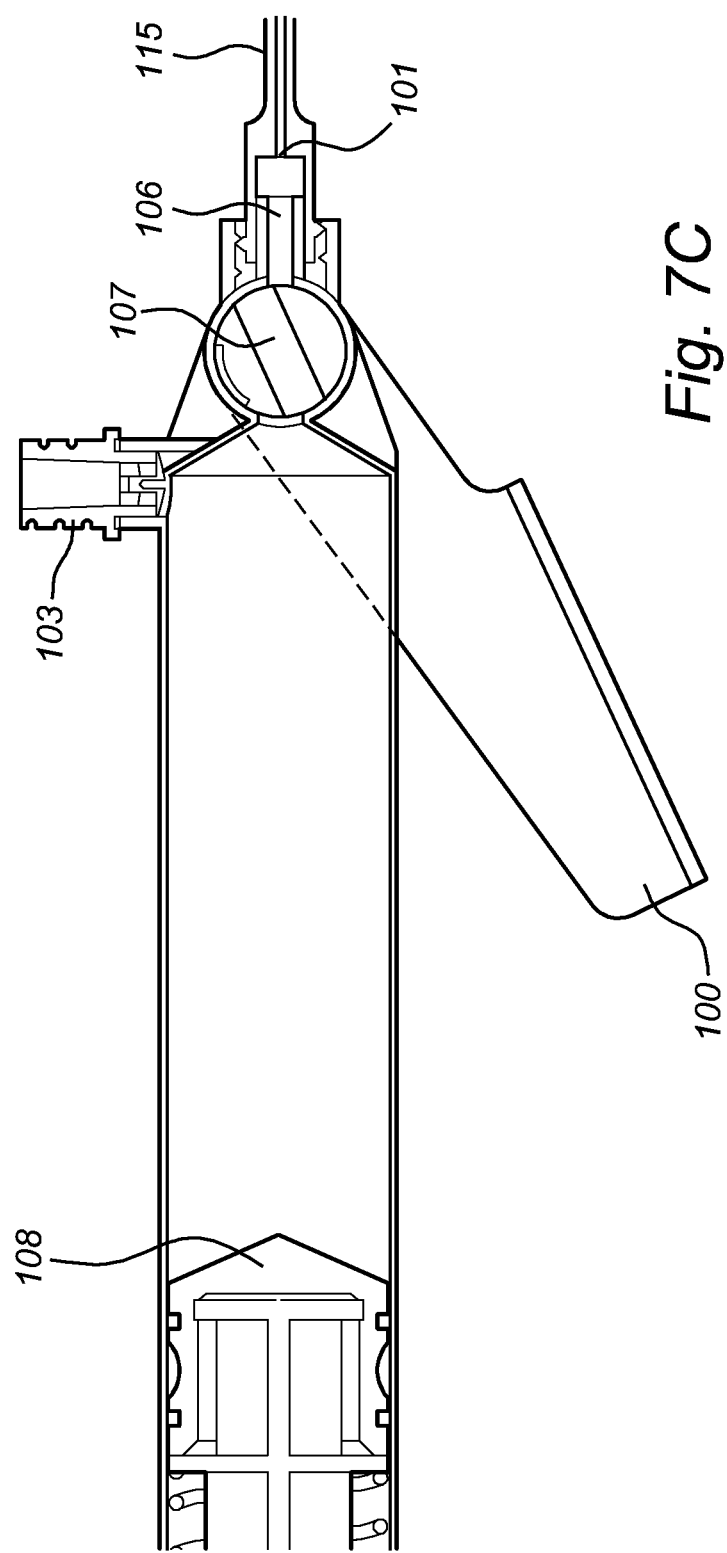
FIG. 7C shows a cross section view of the device shown in FIG. 7A after disconnecting the second device and in an intermediate position.

In use, the user first makes sure that the lumen is in closed position. The user then connects the second device 104 to the device 102 via the connection means 103 as shown in FIG. 7B. The second device 104 comprises the solvent and at least one outlet through which the solvent will be inserted into the single chamber of the device 102. The outlet of the second device is preferably provided with a spring which reinforces the connection between both devices. The user then injects the solvent into the single chamber 109 of the device as shown in FIG. 7B. The injection is performed via the one way valve 110 of the connection means 103. The content of the single chamber will dissolve in the solvent thereby obtaining the Mesna solution. During the injection, the spring piston 108 of the device will be pushed further away from the outlet 101 of the device due to the pressure applied by the solvent entering the single chamber 109. After injection of the desired solvent volume, the second device 104 is disconnected from the device 102. Mesna solution is prevented from flowing out of the connection means due to the presence of the one way valve. The device can be agitated or shacked to further mix the solvent and the solute. Afterwards, the alignment means 100 and thereby the lumen is moved from the closed position to the open position. FIG. 7C and 7C show the lumen in an intermediate position, i.e. between the closed and the open position. Due to said movement, the lumen, the single chamber and the outlet tube are brought in fluid communication with each other. The user can then start dispensing the solution contained inside the single chamber by pushing the spring pistol towards the outlet of the device. The lumen 107 and the lever 100 can preferably be replaced by a valve, such as a trumpet valve or any other suitable valve known to the person skilled in the art. The outlet of the device can be used for direct delivery of the Mesna solution to the target or can be connected to any other suitable device such as a dissector 115 (FIG. 7A and FIG. 7B).

Preferably the device is provided with control means for controlling the volume of the solution flowing out of the device in such a way that each opening of the lumen or the control valve dispenses a predetermined amount of solution.

In a preferred embodiment, the invention provides a method for weakening inter-tissues and/or organs adhesion by delivering a solution comprising at least one solvent and at least one solute to tissues and/or organs. The method comprises the steps of providing a device as described above; moving the lumen of the device from an open position to a closed position thereby interrupting the fluid connection between the single chamber, the lumen and the outlet of the device; connecting a second device containing the solvent to the device via the connection means; injecting a solvent volume into the single chamber of the device thereby dissolving the solute in the solvent and obtaining the solution; disconnecting said second device from the device; moving the lumen from the closed position to the open position thereby creating a fluid connection between the single chamber, the lumen and the outlet of the device; and delivering the obtained solution to said tissues and/or organs by pushing the spring piston towards the outlet of the device. Preferably, the delivery of the solution is performed immediately after obtaining said solution. Preferably, said solute is sodium 2-mercaptoethanesulfonate in powder form.

Figure 8B:
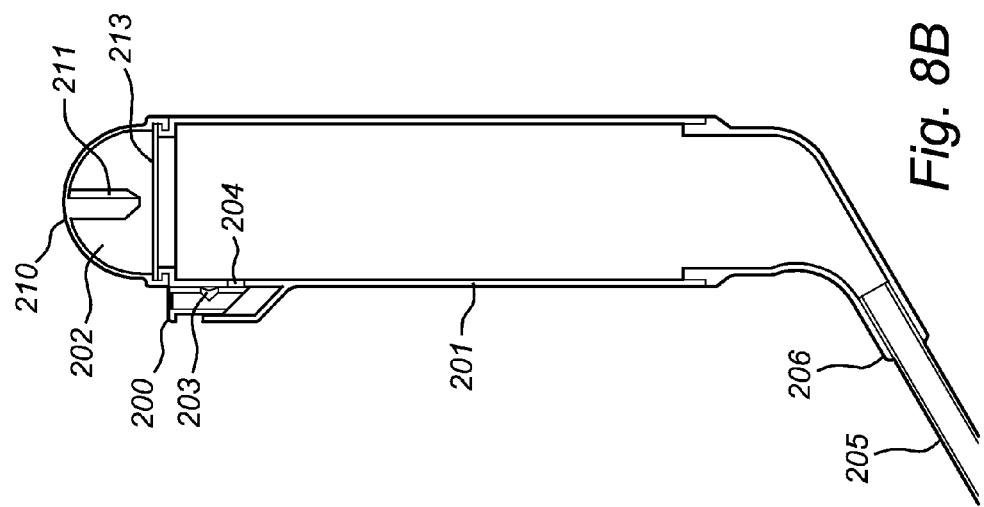
FIG. 8B shows a cross section view of the device shown in FIG. 8A.
Figure 8A:
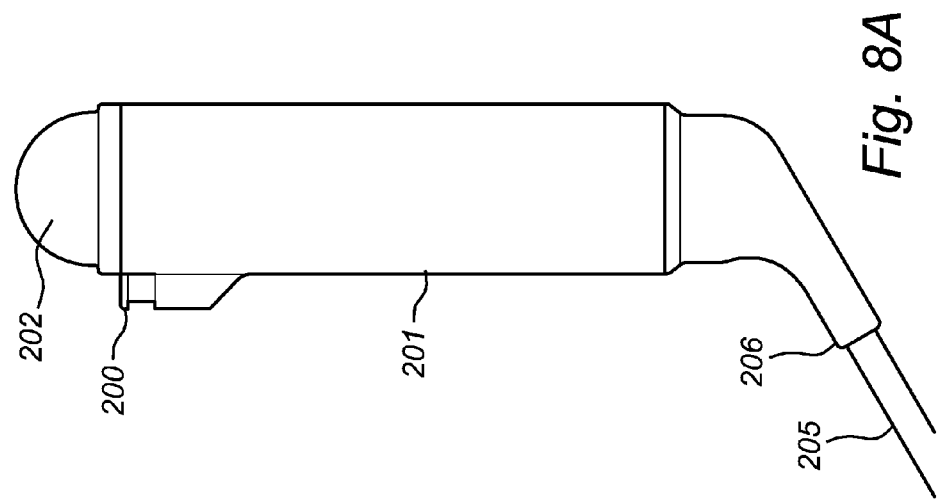
FIG. 8A shows a perspective view of a device according to a fifth embodiment of the invention wherein the air inlet is in closed position.

Referring to FIG. 8A and FIG. 8B, a fifth embodiment of the device is shown. The device comprises a first chamber 202 for housing the solute, i.e. Mesna in powder form; a second chamber 201 for housing the solvent and at least one outlet 206 for delivering the solution. Said outlet is suitable to be in fluid communication with at least one of the chambers. On FIG. 8A and FIG. 8B, the outlet 206 is suitable to be in fluid communication with the second chamber 201. Said outlet can be covered by a removable cap (not shown) when the device is not used. The outlet can be used for direct delivery of the Mesna solution to the target or can be connected to any other suitable device 205.

Figure 8D:
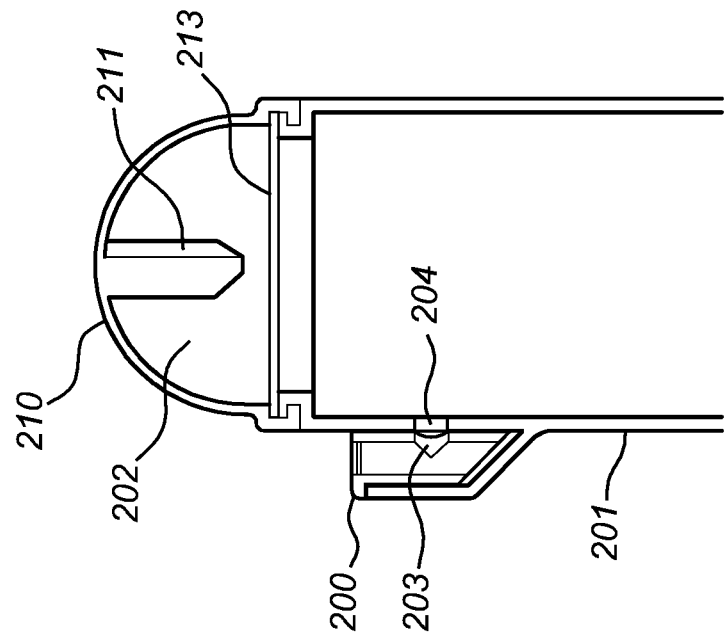
FIG. 8D shows a closer cross section view of the device of FIG. 8A wherein the air inlet is in open position.
Figure 8C:
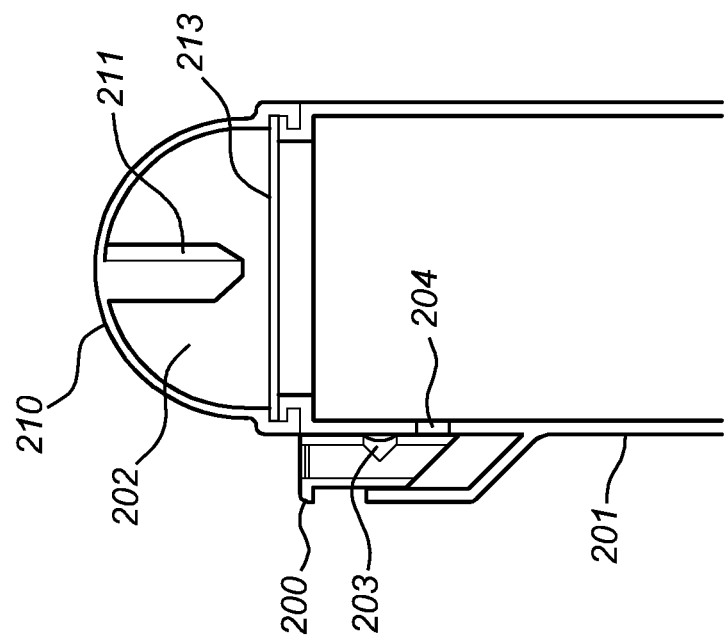
FIG. 8C shows a closer cross section view of the device of FIG. 8A wherein the air inlet is in closed position.
Figure 9:
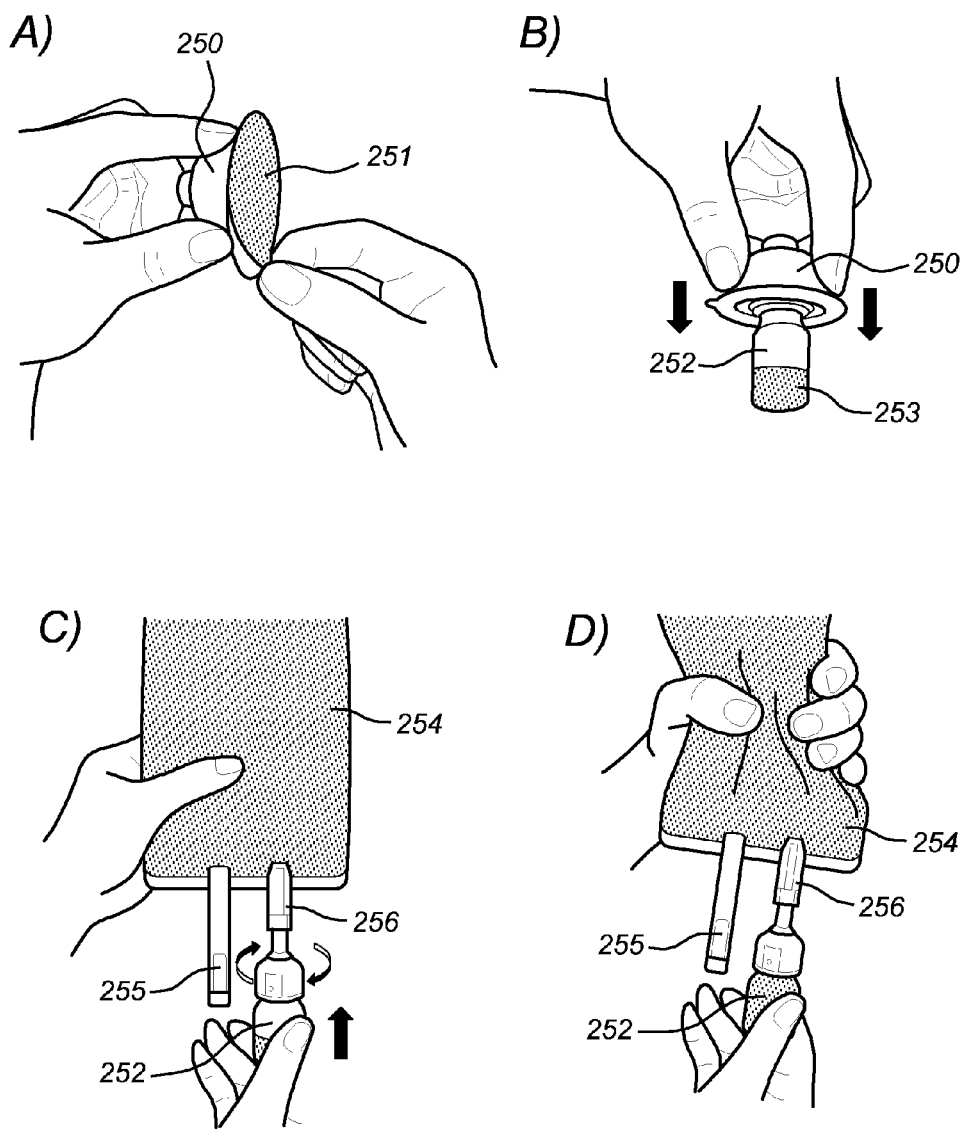
FIG. 9A to G shows the different steps of an embodiment of the use of a mucolytic agent in hydrosurgery.
Figure 9:
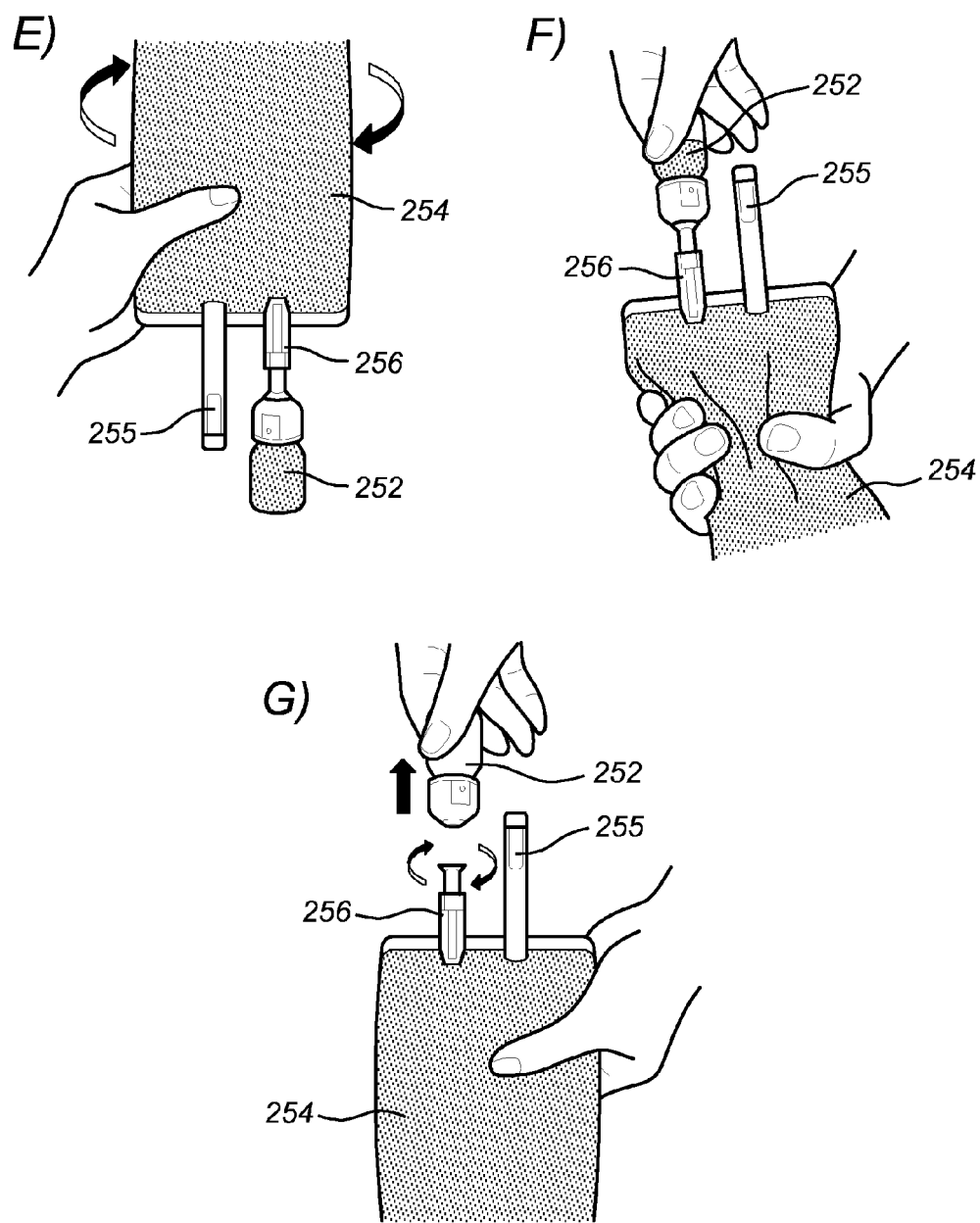

Preferably, the device further comprises a closable air inlet 204. The air inlet is preferably in fluid communication with the chamber comprising the solvent. In a preferred embodiment, the air inlet is closable using the movable closing means 203. Said closing means is movable from an open position in which the air inlet is open such as air can flow in the solvent chamber (FIG. 8C) to a closed position in which the air inlet is closed such as air is prevented from flowing in or outside the solvent chamber (FIG. 8D). The air inlet can be replaced by a one-way valve.

In a preferred embodiment, the first chamber 202 and the second chamber 201 are assembled after being filled with the required solute and the required solvent respectively. The connection can be ensured by a connecting mechanism such as a snap fit system or any other system known to the person skilled in the art. The connecting mechanism keeps the assembled chambers together to ensure maximum efficiency during transfer of product between said first and second chambers. The device is preferably provided with an outer wall surrounding the chambers. Said outer wall can be a film sealed around the chambers thereby ensuring tightness of the device.

Preferably, the first chamber comprises a bottom wall which is a disruptable membrane and the second chamber comprises an upper wall which is a disruptable membrane. Preferably the chambers are assembled such as the disruptable membrane of the first and the second chamber are in contact with each other thereby creating a double barrier 213 also called separation means. This means that the chambers are separated from each other by a double barrier 213. Preferably, the disruptable membranes are made of aluminium laminate.

Preferably, the first chamber 202 is provided with a pressure means 210. Said pressure means is preferably a flexible half cylindrical wall as shown in FIG. 8B. The pressure means is provided with a piercing means 211. The piercing means can be any means known to the person skilled in the art. The pressure means serves the two purposes: breaking the double barrier 213 for reconstituting the solution and expelling the solution out of the device. The pressure means is connected with the piecing means such as when pressing the pressure means, the double barrier 213 is disrupted thereby merging the content of both chambers. The solution is expelled out of the device by applying a manual pressure on said pressure means when the device is in use.

In a preferred embodiment, the solution is delivered in droplets form by applying a manual pressure on pressure means 210. In this embodiment, the control means of the device comprise the pressure means 210. The droplets have a predetermined volume which is of from 50 to 200 µl, preferably from 60 to 150 µl, more preferably from 70 to 100 µl. In this way the user is capable of hand manipulating the device for directly delivering the Mesna solution from the device to the desired location and in desired volumes. The design, the manufacture and the use of the device are simple thereby saving costs and working time. Furthermore, the device offers a possibility to control the amount of fluid flowing out of the device, thereby avoiding any excess of delivered solution volume. In addition, the user will be provided with a control over the time at which the fluid is flowing out of the device. These possibilities are not offered by the devices of the prior art.

Preferably, the remaining first chamber walls and/or the second chamber walls are made of a rigid non-deformable material. Non-deformable material refers to a material that retains its shape when subjected to manual pressure. The non-deformable rigid material allows the first chamber to maintain its intact structure when the chamber bottom wall is being disrupted. The first chamber walls can be made of a plastic material such as a copolymer having hermetic properties allowing a stable and durable conservation of the solute. The rigidity of material also allows an optimal lifetime of the first chamber.

Preferably, said first chamber is provided with a removable cap (not shown) and is preferably provided with a round top. The cap might have a U shape and is produced in a plastic material such as a copolymer. The inner walls of the cap might be threaded in order to be able to screw the cap on the body of the device.

In use, the user makes sure that the air inlet 204 is in closed position. The user removes the cap protecting the first chamber and depresses the pressure means. This leads to the disruption of the double barrier. The content of the first and the second chambers will merge to obtain the solution in which the solute is dissolved in the solvent. The device can be further agitated or shacked to ensure dissolving the solute in the solvent. The air inlet is then opened. The solution can be delivered to the desired location by further applying a pressure on the pressure means acting as a pump of the device as shown in FIG. 8E. Air will be inserted into the second chamber to compensate for the pressure difference inside said chamber after pressing the pressure means and delivering the solution outside the device.

In a preferred embodiment, the invention provides a method for weakening inter-tissues and/or organs adhesion by delivering a solution comprising at least one solvent and at least one solute to tissues and/or organs. The method comprises the steps of providing a device as described above; disrupting the separation means thereby obtaining the solution wherein the solute is dissolved in the solvent; and delivering the obtained solution to said tissues and/or organs; wherein said solute is sodium 2-mercaptoethanesulfonate in powder form. Preferably, the solution is delivered immediately after being obtained in the device.

The present invention further provides for the use of a mucolytic agent in hydrosurgery. Said mucolytic agent is sodium 2-mercaptoethanesulfonate, preferably in powder form. The use of the device and hence the use of a mucolytic agent, i.e. Mesna, in hydrosurgery presents a major advantage. In conventional hydrosurgery methods, it is difficult to apply a pressure which is at the same time sufficient to overcome inter-tissues and/or organs adhesion while avoiding damaging the non-pathologic tissues or organs. The use of Mesna in hydrosurgery allows the use of a lower water pressure while performing the required action, i.e. overcoming inter-tissues and/or inter-cellular adhesion while at the same time preserving the remaining tissues or organs from any damage.

The invention further provides a method and a kit for overcoming inter-tissues and/or inter-cellular adhesion by delivering a solution comprising at least one solvent and at least one solute to tissues and/or organs. The method is preferably a hydrosurgery method comprising the steps of:
  a—connecting a first container comprising the solute to a second container comprising the solvent,
  b—transferring at least partially the content of the first container into the second container thereby dissolving the solute in the solvent and obtaining the solution.

Preferably, the content of the first container is totally transferred to the second container.

c—disconnecting the first container from the second container, and d—delivering the solution obtained in the second container to said tissues and/or organs, wherein said solute is sodium 2-mercaptoethanesulfonate in powder form. In a preferred embodiment, the solvent is saline water wherein the content of NaCl is adjusted to make the solution isotonic. Preferably, delivering the solution is performed immediately after obtaining said solution. Preferably, the method further comprises the step of connecting the container comprising the obtained solution to a delivery control device.

It is to be understood that "solvent reservoir" and "solvent container" are used herein as synonyms.

The different steps of the method are shown in FIG. 9A to FIG. 9G. In a preferred embodiment, the first container 252 containing the solute before being connected to the second container 254 is sealed by a disruptable membrane. Said disruptable membrane is preferably disrupted using a disrupting device enclosed in a blister pack 250. The disrupting device is preferably provided with a piercing means which is preferably covered by a removable foil 251.

In a preferred embodiment, the first container 252 is connected to the second container 254 using at least one connection means 256 such as a luer port which is fixed to the first or to the second container.

In a preferred embodiment, the solvent is at least partially transferred in to the first container 252 thereby dissolving the solute in the transferred solvent volume. Said transferred solute volume in which the solute is dissolved is then transferred back into the second container 254 containing the remaining volume of the solvent; this ensures the transfer of the complete amount of the solute from the first container 252 into the second container 254. These steps can be repeated if necessary.

After disconnecting the first container 252, the second container 254 containing the desired solution is connected to a delivery control device for delivering the solution to the target. Said delivery control device is preferably a high pressure pump. The second container can be provided with an attachment means 255 for removably connecting the delivery control device.

In a preferred embodiment, the first container comprises a high amount of solute. Said amount is from 50 to 600 g of Mesna powder, preferably from 80 to 500 g, more preferably from 90 to 400 g, most preferably from 100 to 350 g of Mesna powder or any value comprised in the mentioned ranges. Preferably, the second container comprises a solvent volume of from 500 ml to 8 L, preferably from 1 L to 7 L, more preferably from 1.5 L to 6 L, most preferably from 2 L to 5 L or any volume comprised within the mentioned ranges.

Figure 10:
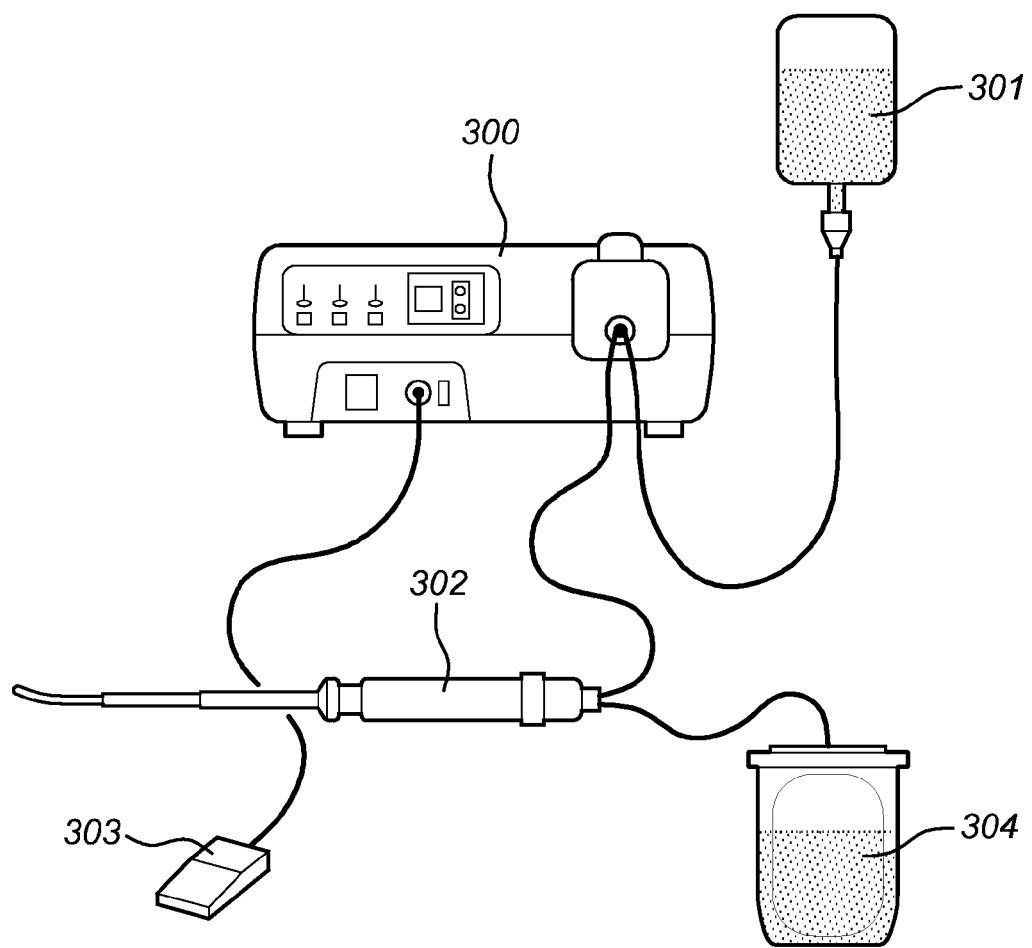
FIG. 10 shows an embodiment of the system wherein a mucolytic agent is used in hydrosurgery.

In a preferred embodiment, the method further comprises the steps of connecting the reservoir or the second container comprising the Mesna solution to a water jet surgery system, and delivering the Mesna solution to a target location. Said delivery is thereby made at high pressure. The delivery means is selected from the group comprising: a surgical device, a high pressure pump, a delivery tube, an applicator or any combination thereof. An embodiment of such connection is shown in FIG. 10 showing the reservoir 301 containing the Mesna solution which is connected to a water jet surgery system. Said system comprises a surgical device 302, an electrically driven mechanical system 300, a pedal 303 connected to said electrically driven mechanical system 300. Preferably a waste container 304 is connected to the surgical device 302 for collecting waste produced during operation.

The present invention further provides a kit comprising at least one first container which is sealed by a disruptable membrane and comprising the solute, at least one second container comprising the solvent and at least one disrupting device. The kit further comprises a leaflet provided with instructions to the user and/or information on the solute and/or the solvent. The first container, the second container, the solvent and the solute are as described above. Said solute is sodium 2-mercaptoethanesulfonate in powder form. In a preferred embodiment, the solvent is saline water wherein the content of NaCl is adjusted to make the solution isotonic.

The present invention further provides for the use of a device and/or method according to any embodiment of the invention, for delivering a solution comprising at least one solvent and at least one solute to a surface wherein said solute is a mucolytic agent in powder form. Preferably, said mucolytic agent is Mesna in powder form. Preferably, the solution consists of one solute and one solvent.

Although the present invention has been described with reference to preferred embodiments thereof, many modifications and alternations may be made by a person having ordinary skill in the art without departing from the scope of this invention which is defined by the appended claims.

What is claimed is:

1. A hydrosurgery method comprising:
   a—connecting a first container comprising a solute to a second container comprising a solvent;
   b—transferring at least partially the content of the first container into the second container thereby dissolving the solute in the solvent and obtaining a solution;
   c—disconnecting the first container from the second container; and
   d—delivering the obtained solution to said tissues and/or organs, wherein said solute is sodium 2-mercaptoethanesulfonate in powder form.

2. A method according to claim 1 further comprising the step of connecting the container comprising the obtained solution to a delivery control device.

3. A method according to claim 1, wherein the solvent is saline water.

4. A method according to claim 2, wherein the delivery control device is a high pressure pump.

* * * * *